United States Patent
Freed et al.

(10) Patent No.: US 11,932,867 B2
(45) Date of Patent: Mar. 19, 2024

(54) METHODS OF TREATING RHEUMATOID ARTHRITIS USING RNA-GUIDED GENOME EDITING OF HLA GENE

(71) Applicant: THE REGENTS OF THE UNIVERSITY OF COLORADO, A BODY CORPORATE, Denver, CO (US)

(72) Inventors: Brian Freed, Aurora, CO (US); Kirsten Anderson, Denver, CO (US); Christina Roark, Englewood, CO (US); Jennifer Matsuda, Denver, CO (US)

(73) Assignees: National Jewish Health, Denver, CO (US); The Regents of the University of Colorado, a Body Corporate, Denver, CO (US)

( * ) Notice: Subject to any disclaimer, the term of this patent is extended or adjusted under 35 U.S.C. 154(b) by 876 days.

(21) Appl. No.: 16/609,175

(22) PCT Filed: Apr. 25, 2018

(86) PCT No.: PCT/US2018/029302
§ 371 (c)(1),
(2) Date: Oct. 28, 2019

(87) PCT Pub. No.: WO2018/200635
PCT Pub. Date: Nov. 1, 2018

(65) Prior Publication Data
US 2020/0199616 A1 Jun. 25, 2020

Related U.S. Application Data

(60) Provisional application No. 62/491,487, filed on Apr. 28, 2017.

(51) Int. Cl.
| | | |
|---|---|---|
| C12N 15/85 | (2006.01) | |
| A61K 35/28 | (2015.01) | |
| A61K 48/00 | (2006.01) | |
| C12N 5/0789 | (2010.01) | |
| C12N 9/22 | (2006.01) | |
| C12N 15/11 | (2006.01) | |

(52) U.S. Cl.
CPC .......... *C12N 15/85* (2013.01); *A01K 67/0275* (2013.01); *A61K 35/28* (2013.01); *C12N 5/0647* (2013.01); *C12N 9/22* (2013.01); *C12N 15/11* (2013.01); *A01K 2217/05* (2013.01); *A01K 2227/105* (2013.01); *A01K 2267/0325* (2013.01); *A61K 48/00* (2013.01); *C12N 2310/20* (2017.05); *C12N 2740/15042* (2013.01); *C12N 2750/14142* (2013.01); *C12N 2800/80* (2013.01)

(58) Field of Classification Search
CPC ...... C12N 15/63; C12N 15/85; C12N 5/0647; C12N 9/22; C12N 15/11; C12N 2310/20; C12N 2740/15042; C12N 2750/14142; C12N 2800/80; C12N 2740/16043; C12N 15/90; C12N 15/113; A61K 35/12; A61K 35/28; A61K 48/00; A61K 48/005; A01K 67/0275; A01K 2217/05; A01K 2227/105; A01K 2267/0325; A61P 19/02; A61P 37/00

See application file for complete search history.

(56) References Cited

U.S. PATENT DOCUMENTS

| | | |
|---|---|---|
| 5,965,787 A | 10/1999 | Luthra et al. |
| 2003/0017143 A1 | 1/2003 | Suciu-Foca |
| 2015/0166616 A1 | 6/2015 | Bancel |

(Continued)

FOREIGN PATENT DOCUMENTS

| | | |
|---|---|---|
| JP | 2004535173 A | 11/2004 |
| WO | 2016201047 A1 | 12/2016 |

(Continued)

OTHER PUBLICATIONS

Ling et al. "HLA-DRB1 amino acid positions 11/13, 71, and 74 are associated with inflammation level, disease activity, and the health assessment questionnaire score in patients with inflammatory polyarthritis." Arthritis & Rheumatology 68.11 (2016): 2618-2628. (Year: 2016).*

(Continued)

*Primary Examiner* — Janet L Epps-Smith
*Assistant Examiner* — Alexander W Nicol
(74) *Attorney, Agent, or Firm* — Womble Bond Dickinson (US) LLP

(57) ABSTRACT

Methods of preventing or treating rheumatoid arthritis (RA) in a subject by introducing the DRB1*04:01$^{K71E}$ mutation that is resistant to RA. The resistant allele is introduced into the subject having or at risk of developing RA, using a HLA CRISPR/Cas9 vector that targets codon 71 in the HLA allele DRB1*04:01, introducing a single A to G point mutation in codon 71 by homology directed repair to alter the lysine at position 71 of the expressed protein to glutamic acid. This modified allele is affected in the subject's hematopoietic stem cells, which are then expanded and transplanted back into the patient. This microgene therapy confers RA-resistance via an autologous transplant. The invention includes isolated nucleic acids, vectors, recombinant viruses, cells, and pharmaceutical compositions to modify the HLA DRB1*04:01 allele.

5 Claims, 4 Drawing Sheets

Specification includes a Sequence Listing.

(56) References Cited

U.S. PATENT DOCUMENTS

| | | | |
|---|---|---|---|
| 2018/0296603 A1* | 10/2018 | Gori | C12N 5/0647 |
| 2020/0199616 A1 | 6/2020 | Freed | |
| 2021/0071249 A1 | 3/2021 | Irani | |
| 2023/0091257 A1 | 3/2023 | Freed | |

FOREIGN PATENT DOCUMENTS

| | | |
|---|---|---|
| WO | 2017/044672 | 3/2017 |
| WO | 2018200635 | 11/2018 |
| WO | 2019/126818 | 6/2019 |
| WO | 2019/158602 | 8/2019 |
| WO | 2020/006357 | 1/2020 |
| WO | 2020/180501 | 9/2020 |
| WO | 2020/181062 | 9/2020 |
| WO | 2020/181272 | 9/2020 |
| WO | 2020/201467 | 10/2020 |

OTHER PUBLICATIONS

Extended European Search Report for EP 18791113.6 dated Mar. 10, 2021, 8 pages.
Anderson, Kirsten M., "A Molecular Analysis of the Shared Epitope Hypothesis: Binding of Arthritogenic Peptides to DRB1*04 Alleles 11", Arthritis & Rheumatology, vol. 68, No. 7, Jul. 2016, pp. 1627-1636.
Roark, C. et al., "Progress towards gene editing of HLA-DRB1*04:01 by CRISPR/Cas9", Human Immunology, vol. 79, No. Suppl., P162, 31 (Aug. 31, 2018), p. 186.
Roark, C. L. et al., "Arthritogenic peptide binding to DRB1*01 alleles correlates with susceptibility to rheumatoid arthritis", Journal of Autoimmunity, vol. 72, Apr. 30, 2016 (Apr. 30, 2016), pp. 25-32.
Office Action dated Apr. 5, 2022 in connection with Japanese patent application No. 2019-558446, 6 pages with English translation.
Anderson, Kirsten M. "A Molecular Analysis of the Shared Epitope Hypothesis," Arthritis & Rheumatology, vol. 68, No. 7, Jul. 2016, pp. 1627-1636, 11 pages.
National Center for Biotechnology Information, "Amycolatopsiskeratiniphila strain FH 1893 genome assembly, chromosone: I", GenBank: LT629789, Oct. 21, 2016, 499 pages.
National Center for Biotechnology Information, "Microlunatus phosphovorus NM-1 DNA, complete genome", GenBank: AP012204.1, Oct. 7, 2016, 746 pages.
National Center for Biotechnology Information, "Myodes glareolus MHC class II antigen (Mygl-DRB) gene, Mygl-DRB*48 allele, exon 2 and partial cds", GenBank: GQ901819.1, Jul. 24, 2016, 1 pages.
PCT, "International Search Report and Written Opinion", Application No. PCT/US2018/029302, dated Sep. 11, 2018, 15 pages.
Raychaudhuri, Soumya et al., "Five amino acids in three HLA proteins explain most of the association between MHC and seropositive rheumatoid arthritis", Nat. Genet.; vol. 44 No. 3, Mar. 2012, pp. 291-296.
PHla 3D, HLA Molecule DRB1*04:01, retrieved online at https://www.phla3d.com.br/alleles/view/DRB1*04:01/1, Apr. 17, 2023.
HLA Nomenclature, HLA Alleles Numbers, retrieved online at http://hla.alleles.org/nomenclature/stats.html, Apr. 17, 2023.

Coppin et al., "Position 71 in the α helix of the DRB domain is predicted to influence peptide binding and plays a central role in allorecognition", European Journal Immunology, 23, 343-349, 1993.
Young et al., "HLA-DRB1 amino acid disparity is the major stimulus of interleukin-2 production by alloreactive helper T-lymphocytes", Immunogenetics, 47, 310-317, 1998.
Fleischhauer et al., "Bone Marrow—Allograft Rejection by T Lymphocytes Recognizing a Single Amino Acid Difference in HLA-B44", The New England Journal of Medicine, 323:1818-1822, Dec. 27, 1990.
Schulman et al., "Mismatches at the HLA-DR and the HLA-B Loci Are Risk Factors for Acute Rejection after Lung Transplantation", American Journal of Respiratory and Critical Care Medicine, vol. 157, 1833-1837, 1998.
McInnes et al., "The Pathogenesis of Rheumatoid Arthritis", The New England Journal of Medicine, 365: 2205-2219, Dec. 8, 2011.
Diller, R. et al., "Metal-triggered conformational reorientation of a self-peptide bound to a disease-associated HLA-B*27 subtype", J. Biol. Chem., Jul. 2019, vol. 294 (36), pp. 13269-13279.
Dever et al., "CRISPR / Cas9 (Beta)-globin gene targeting in human haematopoietic stem cells", Nature, vol. 539, pp. 384-389, Nov. 17, 2016.
Hoban et al., "CRISPR / Cas9-Mediated Correction of the Sickle Mutation in Human CD34+ cells", Molecular Therapy, vol. 24, No. 9, pp. 1561-1569, Sep. 2016.
Pommie et al., "IMGT standardized criteria for statistical analysis of immunoglobulin V-REGION amino acid properties"; Journal of Molecular Recognition 2004; 17; pp. 17-32 (Year: 2004).
Watanabe et al., STN Accession No. 20200609125 (abstract for Watanabe et al., 2020, 4 pages) (Year: 2020).
International Search Report and Written Opinion for International Application No. PCT/US2022/028643, dated Oct. 11, 2022.
International Search Report and Written Opinion for International Application No. PCT/US2022/028644, dated Oct. 11, 2022.
International Search Report and Written Opinion for International Application No. PCT/US2022/028645, dated Dec. 2, 2022.
Zubillaga et al., "HLA-DQA1 and HLA-DQB1 genetic markers and clinical presentation in celiac disease", Journal of Pediatric Gastroenterology and Nutrition, Lippincott Williams Wilkins, Inc, US, vol. 34, No. 5, May 1, 2002, pp. 548-554.
Percival D Sampaio-Barros et al., "Characterization and outcome of uveitis in 350 patients with spondyloarthropathies", Rheumatology International; Clinical and Experimental Investigations, Springer, Berlin, DE, vol. 26, No. 12, Sep. 7, 2006), pp. 1143-1146.
Misra et al., "Structure-based selection of human metabolite binding P4 pocket of DRB1*15:01 and DRB1*15:03, with implications for multiple sclerosis", Genes and Immunity, Nature Publishing Group, GB, vol. 20, No. 1, Jan. 20, 2018, pp. 46-55.
Misra et al., "The immunogenetics of neurological disease", Immunology, Wiley-Blackwell Publishing LTD, GB, vol. 153, No. 4, Dec. 11, 2017, pp. 399-414.
Ryan et al., "Genetic markers of treatment response to tumour necrosis factor-[alpha] inhibitors in the treatment of psoriasis", Clinical and Experimental Dermatology, Blackwell Scientific Publications, GB, vol. 39, No. 4, Apr. 23, 2014, pp. 519-524.
Johannes R Hov et al., "Electrostatic modifications of the human leukocyte antigen-DR P9 peptide-binding pocket and susceptibility to primary sclerosing cholangitis", Hepatology, John Wiley & Sons, Inc, US, vol. 53, No. 6, May 13, 2011, pp. 1967-1976.

* cited by examiner

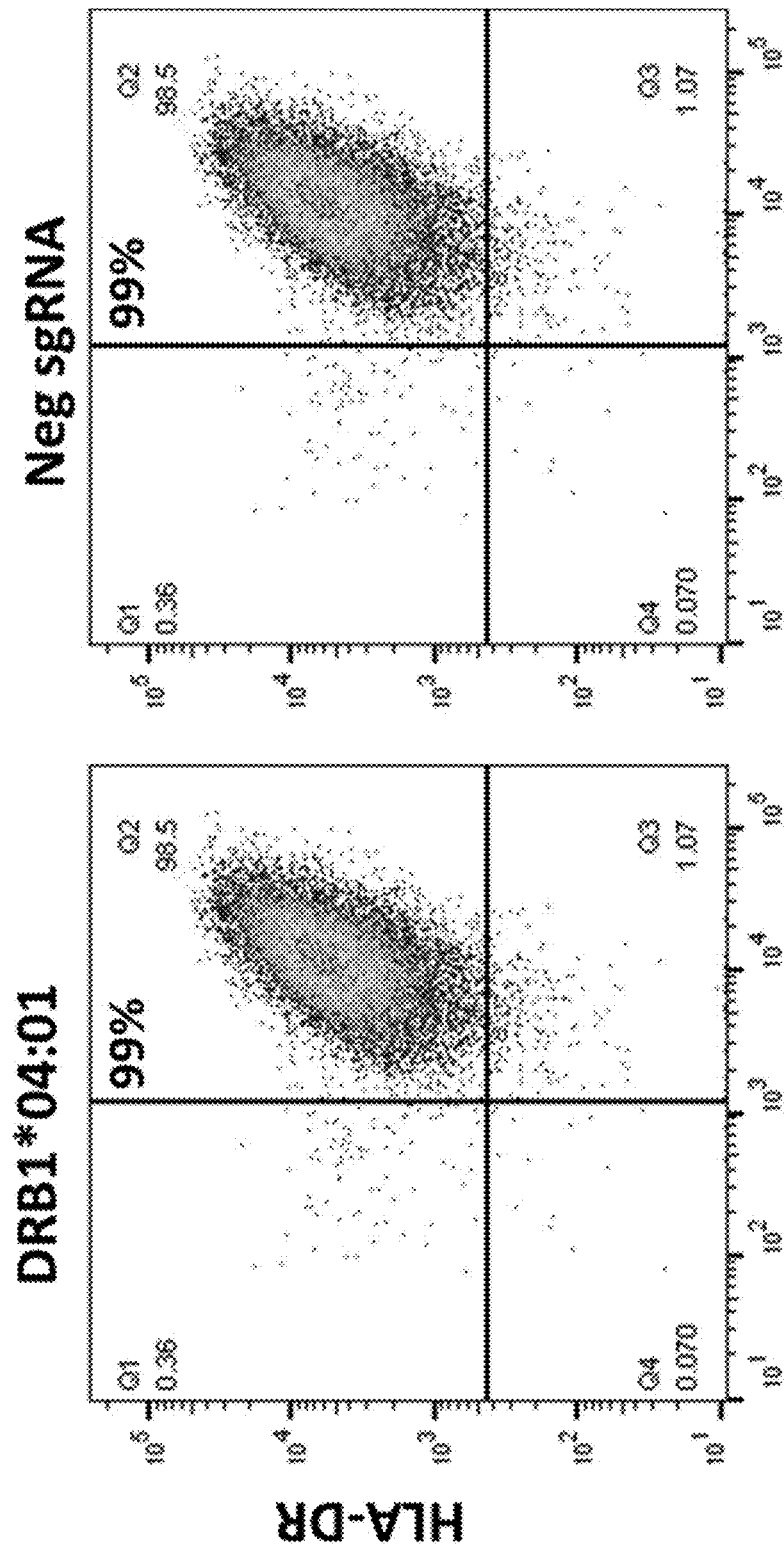

METHODS OF TREATING RHEUMATOID ARTHRITIS USING RNA-GUIDED GENOME EDITING OF HLA GENE

CROSS-REFERENCE TO RELATED APPLICATIONS

This application is a national stage application under 35 U.S.C. § 371 of International Application No. PCT/US2018/029302, filed Apr. 25, 2018, entitled "Methods of Treating Rheumatoid Arthritis Using RNA-Guided Genome Editing of HLA Gene," which claims priority to and the benefit of U.S. Provisional Patent Application Ser. No. 62/491,487, filed Apr. 28, 2017, the entire disclosures of which are incorporated herein in their entirety by reference.

BACKGROUND

Rheumatoid arthritis (RA) is a chronic disease characterized by autoimmune destruction of joints and surrounding tissues. Susceptibility to the disease has several genetic components, but the HLA-DRB1 locus is clearly the most significant (Barton A, Worthington J. Genetic susceptibility to rheumatoid arthritis: an emerging picture. Arthritis Rheum 2009; 61:1441-46). Several DR4 alleles, notably, DRB1*04:01, *04:04, and *04:05, are strongly associated with RA, while DRB1*04:02 is not (the alleles are designated by the newly accepted World Health Organization nomenclature [hla.alleles.org], whereby the family and alleles are separated by a colon; thus, DRB1*04:01 corresponds to DRB1*0401 in earlier literature). In addition, DRB1*01:01, *01:02, *10:01, and *14:02 have sometimes been associated with RA, particularly in non-Europeans. These disparate alleles have been hypothesized to contribute to RA via the presence of a "shared epitope," a common set of amino acids at positions 70-74 of the peptide-binding groove. Peptide binding to HLA-DRB1 molecules is controlled by 6 pockets, each with multiple polymorphic amino acids that create millions of potential peptide binding epitopes. Seemingly disparate HLA alleles (e.g., DRB1*04:01 and *16:02) can share an epitope that closely related alleles (e.g., DRB1*04:01 and *04:02) do not. The concept of a shared epitope in susceptibility to RA is now widely accepted, although the exact nature of the epitope and its role in the disease has been the subject of considerable debate (Zanelli E, Breedveld F C, de Vries R R. HLA class II association with rheumatoid arthritis: facts and interpretations. Hum Immunol. 2000; 61:1254-61; Weyand C M, Goronzy J J. Association of MHC and rheumatoid arthritis: HLA polymorphisms in phenotypic variants of rheumatoid arthritis. Arthritis Res 2000; 2:212-16). The presence of aspartic acid at position 70 (D70) alone has been reported to have a protective effect (Mattey D L, Dawes P T, Gonzales-Gay M A, Garcia-Porrua C, Thomson W, Hajeer A H, et al. HLA-DRB1 alleles encoding an aspartic residue at position 70 protect against development of rheumatoid arthritis. J Rheumatol 2001; 28:232-39), and positions outside residues 70-74 have also been implicated in the disease (Debaz H, Olivo A, Vasquez Garcia M N, de la Rosa G, Hernandez A, Lina L, et al. Relevant residues or DR1 third hypervariable region contributing to the expression and to severity of rheumatoid arthritis (RA) in Mexicans. Hum Immunol 1998; 59:287-94; De Vries N, Tijssen H, van Riel P L, van de Putte L B. Reshaping the shared epitope hypothesis: HLA-associated risk for rheumatoid arthritis is encoded by amino acid substitutions at positions 67-74 of the HLA-DRB1 molecule. Arthritis Rheum 2002; 46:921-28). However, very little is known about how these epitopes bind citrullinated autoantigens that are associated with RA in most patients.

The present inventors have shown that relatively few amino acids in DRB1*04:01 are associated with rheumatoid arthritis in humans (Freed et al., Arthritis Rheum 2011; 63(12):3733-39), and that one of these (position 71) can alter peptide binding to make a susceptible allele function like a resistant one. (Anderson K M, Roark C L, Portas M, Aubrey M T, Rosloniec E F, Freed B M. A Molecular Analysis of the Shared Epitope Hypothesis: Binding of Arthritogenic Peptides to DRB1*04 Alleles. Arthritis Rheumatology 68:1627-36, 2016; Roark C L, Anderson K M, Aubrey M T, Rosloniec E F, Freed B M. Arthritogenic peptide binding to DRβ1*01 alleles correlates with susceptibility to rheumatoid arthritis. J Autoimmunity 72:25, 2016).

The approval in Europe of the first gene therapy obtained by uniQuire BV for alipogenic tiparvovec (trade name GLYBERA™) to treat lipoprotein lipase (LPL) deficiency was a milestone in the quest to bring gene-based therapeutics into clinical use. Tiparvovec (AAV1-LPL(S447X)) incorporates an intact human LPL gene variant, i.e. LPL (Ser447X), in an adeno-associated virus (AAV) vector, which is delivered intramuscularly (Gaudet D, Méthot J, Déry S, et al. Efficacy and long-term safety of alipogene tiparvovec (AAV1 LPL(S447X)) gene therapy for lipoprotein lipase deficiency: an open-label trial. Gene Ther. Jun. 21, 2012).

Use of autologous cells engineered with viral elements or nucleases capable of genomic editing may permit greater safety than intravenous delivery of targeted virus. Ex vivo protocols allow for screening of the genomes of manipulated cells to assess the frequency or viral insertions, double strand breaks in DNA (DSBs) or other potentially mutagenic events (Li H, Haurigot V, Doyon Y, et al. In vivo genome editing restores haemostasis in a mouse model of haemophilia. Nature. 475(7355):217-21, 2011). Therapeutically relevant levels of genetically modified stem cells needed to effect clinical outcomes may be more readily achieved by expansion of large populations of cells ex vivo and reintroduction(s) into the patient.

Bacterial and archaeal CRISPR systems rely on crRNAs in complex with Cas proteins to direct degradation or modification of complementary sequences present within invading viral and plasmid DNA. In vitro reconstitution of the S. pyogenes type II CRISPR system relies on crRNA fused to a normally trans-encoded tracrRNA, that is sufficient to direct Cas9 protein to sequence-specifically cleave target DNA sequences matching the crRNA.

The chronic inflammatory nature of RA can cause damage to a wide variety of body systems, including the joints, bones, skin, eyes, lungs, heart and blood vessels. While new types of medications have improved treatment options dramatically, severe rheumatoid arthritis can still cause physical disabilities. Thus, there is a critical need to identify ways to avoid the development of RA and to abate the inflammatory response of this incurable autoimmune disease.

SUMMARY

The present inventors have discovered that a single amino acid residue at position 71 in the HLA DRB1*04:01 allele accounts for the difference in peptide binding between the DRB1*04:01 allele (the gene associated with susceptibility to rheumatoid arthritis) and the DRB1*04:02 allele (the gene that confers resistance to rheumatoid arthritis). The invention includes methods of treating a human subject with rheumatoid arthritis (RA) by selectively targeting and replacing a portion of the subject's genomic DRB1*04:01 gene sequence containing a lysine at position 71 in the gene with a replacement sequence containing a glutamic acid at this position. The resultant, modified DRB1 gene, upon expression, confers resistance to RA in the subject, compared to the wild type (non-modified DRB1 gene encoding a lysine at position 71).

Thus, this disclosure provides methods of modifying a eukaryotic cell with a three-component system including guide RNA complementary to genomic DNA, and an enzyme that interacts with the RNA, and a template nucleic acid that contains at least a portion of the genomic DNA. The guide RNA and the enzyme are expressed by the cell. The guide RNA of the RNA/enzyme complex binds to complementary genomic DNA and cleaves the genomic DNA. The enzyme cleaves genomic sequences targeted by the guide RNA sequences. A portion of the template nucleic acid is substituted into the genomic DNA, thereby creating a genome-altered eukaryotic cell. The genomic alteration may be an insertion, a deletion, or a substitution of a nucleotide sequence, including, preferably a substitution of a single nucleotide in the targeted genomic DNA. The genomic sequences targeted by the guide RNA sequences may be human leukocyte antigen (HLA) genomic DNA sequences. The HLA gene sequences may be an HLA-DRB1 gene allele that encodes the HLA class II histocompatibility antigen, DRB1 beta chain protein.

These methods may include transfecting the eukaryotic cell with a nucleic acid encoding guide RNA complementary to genomic DNA of the eukaryotic cell, and transfecting the eukaryotic cell with a nucleic acid encoding an enzyme that interacts with the guide RNA and cleaves the genomic DNA in a site-specific manner, and transfecting the cell with the template nucleic acid, such that the cell expresses the guide RNA and the enzyme, the guide RNA binds to complementary genomic DNA, the enzyme cleaves the genomic DNA in a site-specific manner, and at least a portion of the nucleic acid template is substituted into the targeted genomic DNA to create a genome-altered eukaryotic cell. These methods may include genetically altering the eukaryotic cell by introducing the nucleic acid encoding the guide RNA complementary to genomic DNA into the genome of the cell. Alternatively or additionally, these methods may include genetically altering the eukaryotic cell by introducing a nucleic acid encoding an enzyme that cleaves the genomic DNA, into the genome of the cell. Alternatively or additionally, these methods may include genetically altering the eukaryotic cell by introducing a nucleic acid encoding the template DNA into the cell. Any one, or any combination, of the nucleic acid molecules encoding the guide RNA complementary to genomic DNA, the enzyme that cleaves the genomic DNA, and/or the template DNA may be transfected into the cell. Similarly, any one, or any combination, of the nucleic acid molecules encoding the guide RNA complementary to genomic DNA, the enzyme that cleaves the genomic DNA, and/or the template DNA may be inserted into the genome of the cell.

In these methods, the RNA complementary to genomic DNA may include between about 10 nucleotides to about 250 nucleotides, or between about 20 nucleotides to about 100 nucleotides. In these methods, the enzyme may perform a desired function, such as cleavage of genomic DNA and/or substitution of a portion of the template nucleic acid into the targeted genomic DNA, in a site-specific manner when the guide RNA is hybridized to the complementary genomic DNA. In these methods, the guide RNA and the enzyme are preferably components of a bacterial Type II CRISPR system. In these methods, the enzyme is preferably a Cas9, or modified Cas9, or a homolog of Cas9 enzyme. In these methods, the eukaryotic cell may be a yeast cell, a plant cell, or a mammalian cell. The eukaryotic cell is preferably a human cell. The human cell may be a primary blood cell, or is a population of blood cells. The human cell may be a hematopoietic stem/progenitor cell (HSCs). In these methods, the eukaryotic cell may be selected from a circulating blood cell, a mobilized blood cell, a bone marrow cell, a myeloid progenitor cell, a multipotent progenitor cell, and a lineage restricted progenitor cell.

In these methods, the guide RNA molecule may comprise a targeting domain which is complementary to a target domain in a HLA DRB1*04:01 locus. The guide RNA may comprise a ribonucleic acid containing at least one modified nucleotide selected from the group consisting of pseudouridine, 5-methylcytodine, 2-thio-uridine, 5-methyluridine-5'-triphosphate, 4-thiouridine-5'-triphosphate, 5,6-dihydrouridine-5'-triphosphate, and 5-azauridine-5'-triphosphate. The guide RNA may comprise the nucleotide sequence GGACCUCGUCUUCGCCCGGCGCC (SEQ ID NO:1). The guide RNA sequence may be a tracrRNA-crRNA fusion, in which case, the crRNA may comprise the nucleotide sequence GGACCUCGUCUUCGCCCGGCGCC (SEQ ID NO:1).

In these methods, the template nucleic acid may comprise a nucleotide sequence complementary to the HLA-DRB1 allele. The template nucleic acid may comprise a nucleotide sequence of the HLA-DRB1*04:01 allele comprising an A to T point mutation at codon 71. The template nucleic acid substituted into the HLA-DRB1 locus may encode a glutamic acid at position 71 of the DRB1*04:01 allele. The template nucleic acid may be a nucleotide sequence beginning with G and immediately precedes an NGG motif recognized by the Cas enzyme. The template nucleic acid may be a single stranded oligodeoxynucleotide (ssODN). The ssODN may comprise a 5' phosphorothioate modification, and/or a 3' phosphorothioate modification, and/or both a 5' phosphorothioate modification and a 3' phosphorothioate modification.

In these methods, the guide RNA molecule and the Cas9 polypeptide may be introduced into the cell as a pre-formed ribonucleotide complex. Alternatively or additionally, the Cas9 molecule may be introduced into the cell as a nucleic acid encoding a Cas9 protein. Alternatively or additionally, the guide RNA may be introduced into the cell as a nucleic acid encoding the guide RNA, and the Cas9 protein may be introduced into the cell as a nucleic acid encoding the Cas9 protein, and the cell expresses the guide RNA and the Cas9 protein. In these methods, the guide RNA, the Cas9 protein, and the template nucleic acid may be introduced into the cell within an adeno-associated virus (AAV) or an integration deficiency lentivirus (ILDV).

These methods may include expanding the cell ex vivo after the introducing steps to form an isolated population of cells comprising the HLA-DRB1 allele, or portion thereof, encoded by the template nucleic acid, substituted into the targeted genomic DNA. These methods may further include administering the population of cells to a subject as an autologous bone marrow transplant.

This disclosure also provides an isolated mammalian blood cell which comprises one or more genomic modifications in an HLA gene. The genomic modification may be an insertion, a deletion, or a substitution of a nucleotide sequence, including, preferably a substitution of a single nucleotide in the targeted genomic DNA. The genomic modification may be in the human leukocyte antigen (HLA)

genomic DNA sequences. The modified HLA gene sequence may be an HLA-DRB1 gene allele. The genetic modification may comprise a nucleotide sequence of the HLA-DRB1 allele comprising an A to T point mutation at codon 71. The genetic modification may comprise a DNA sequence encoding a glutamic acid at position 71 of the DRB1*04:01 locus.

The genetically-modified isolated mammalian blood cell may be a primary blood cell, or is a population of blood cells, or a hematopoietic stem/progenitor cell (HSCs), or a blood cell selected from the group consisting of a circulating blood cell, a mobilized blood cell, a bone marrow cell, a myeloid progenitor cell, a multipotent progenitor cell, and a lineage restricted progenitor cell. These genetically-modified isolated mammalian blood cells may be produced by the methods of modifying a eukaryotic cell with a three-component system, described above.

This disclosure also provides compositions comprising these genetically-modified, isolated mammalian blood cells. These compositions may be pharmaceutical compositions useful in methods of treating or preventing rheumatoid arthritis in a subject by administering the genetically-modified, isolated mammalian blood cells, or the compositions containing them, to a subject in need of such treatment.

This disclosure also provides a single Cas nuclease in a complex with the guide RNA comprising a CRISPR-activating RNA (crRNA) including an HLA-DRB1-specific protospacer domain. The crRNA may be a trans-activating RNA (tracrRNA) or may comprise an artificial chimeric single-guide-RNA (sgRNA) comprising the crRNA linked to the tracrRNA. The crRNA may comprise the nucleotide sequence GGACCUCGUCUUCGCCCGGCGCC (SEQ ID NO:1). The crRNA may include an HLA-DRB1-specific protospacer domain of about 17 nucleotides to about 20 nucleotides. The crRNA may also be linked to a tracrRNA-binding domain comprising from about 12 nucleotides about 20 nucleotides. The crRNA may also comprise at least one chemical modification selected from a chemically-modified nucleotide having a modification selected from a ribose modification, an end-group modification, and an internucleotide linkage modification. The crRNA may also comprise a ribonucleic acid containing at least one modified nucleotide selected from the group consisting of pseudouridine, 5-methylcytodine, 2-thio-uridine, 5-methyluridine-5'-triphosphate, 4-thiouridine-5'-triphosphate, 5,6-dihydrouridine-5'-triphosphate, and 5-azauridine-5'-triphosphate.

This disclosure also provides vectors comprising a polynucleotide encoding the Cas9 nuclease, and guide RNA that mediates the binding of the Cas9 nuclease to an HLA-DRB1 gene. In these vectors, the guide RNA sequence may encode a tracrRNA-crRNA fusion. The vector may be an adenovirus vector, or an integration-deficient lentiviral vector (IDLV), or an integration-deficient foamyviral vector (IDFV).

This disclosure also provides methods of treating or preventing rheumatoid arthritis in a subject including introducing into a cell of the subject a guide RNA sequence that is complementary to a target nucleic acid sequence within an HLA-DRB1 locus, and introducing into the cell of the subject a Cas9 protein, and introducing into the cell of the subject a template nucleic acid comprising at least a portion of an HLA-DRB1 allele. In the cell of the subject, the guide RNA sequence binds to the target nucleic acid sequence and the Cas9 protein cleaves the target nucleic acid sequence, and a portion of the HLA-DRB1 allele is substituted into the target nucleic acid. The cell of the subject is thereby genetically modified by an insertion, a deletion, or a substitution of a nucleotide sequence, including, preferably, a substitution of a single nucleotide into the targeted genomic HLA-DRB1 allele. The genetic modification may comprise a nucleotide sequence of the HLA-DRB1 allele comprising an A to T point mutation at codon 71. The genetic modification may comprise a DNA sequence encoding a glutamic acid at position 71 of the DRB1*04:01 allele.

In these methods of treating or preventing rheumatoid arthritis in a subject, the guide RNA, the Cas 9 protein, and the template nucleic acid may be introduced into the cell through viral transduction. The guide RNA, the Cas 9 protein, and the template nucleic acid may be introduced ex vivo into a cell that has been isolated from the subject. The genetically modified cells in which a portion of the HLA-DRB1 allele is substituted into the target nucleic acid may be administered to the subject as an autologous bone marrow transplant.

This disclosure also provides methods of manufacturing a medicament comprising a genetically modified cell of this disclosure for the treatment or prevention of rheumatoid arthritis.

This disclosure also provides methods of using a genetically modified cell of this disclosure, or a composition comprising those cells, for the treatment or prevention of rheumatoid arthritis.

Further embodiments will be evident to the skilled artisan upon a reading of the present specification.

BRIEF DESCRIPTION OF THE FIGURES

FIGS. 3A-3D show flow cytometry results sorting for cells that have lost HLA-DR expression in in vitro transfection efficiency analysis using CRISPR constructs of this disclosure. FIG. 3A shows flow cytometry results for T2 cells expressing DRB1*04:01 that were not transfected, and FIG. 3B shows flow cytometry results for T2 cells expressing DRB1*04:01 that were transfected using scrambled RNA. FIG. 3C shows flow cytometry results for T2 cells expressing DRB1*04:01 that were transfected 208/fwd guide RNA of this disclosure, and FIG. 3D shows flow cytometry results for T2 cells expressing DRB1*04:01 that were transfected 185/rev guide RNA of this disclosure.

DETAILED DESCRIPTION

Figure 1:
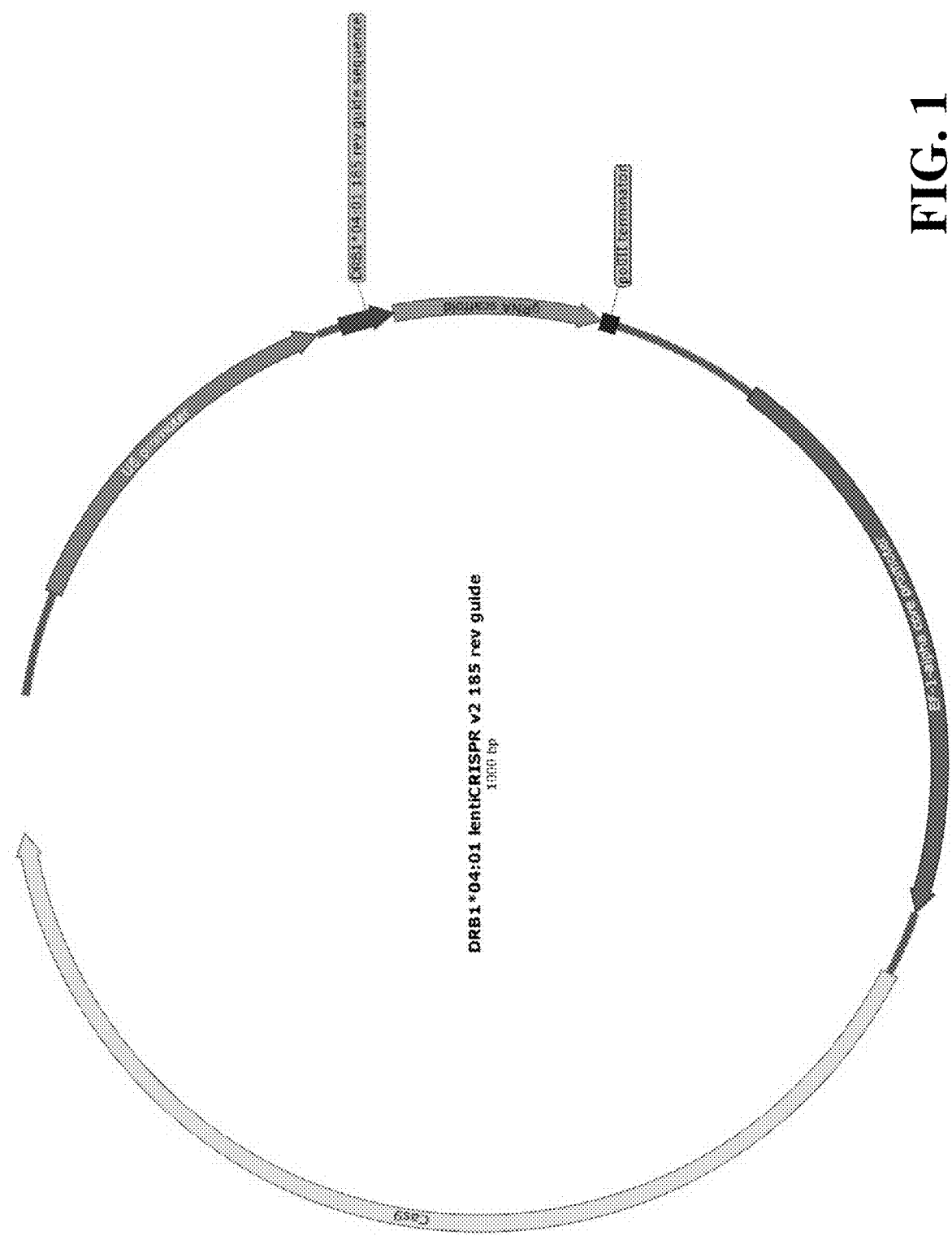
FIG. 1 is a map of a lentiviral plasmid encoding a DRB1*04:01 guide sequence of this disclosure.

This disclosure provides a method of treating a subject with rheumatoid arthritis (RA) by selectively targeting and replacing a portion of the subject's HLA DRB1 gene sequence containing a lysine at amino acid 71 of the HLA DRB1*04:01 allele with a replacement sequence. The resultant, modified DRB1 gene, containing the replacement sequence, upon expression, confers resistance to the development and progression of RA in the subject compared to a subject having the HLA DRB1*04:01 allele. Preferably, the presence of the modified HLA DRB1*04:01 are adequate to obviate or reduce the need for medication or other RA treatments in the subject, similar to a subject having the HLA DRB1*04:02 allele.

The disclosure provides a method of treating RA in a subject by introducing into a cell of the subject one or more nucleic acids encoding a nuclease that targets a portion of the human leukocyte antigen (HLA)-DRB1 gene containing an allele associated with RA, wherein the nuclease creates a double stranded break in the DRB1 gene; a guide RNA molecule comprising a nucleotide sequence complementary to a target nucleic acid sequence within HLA-DRB1 locus; and an isolated template nucleic acid comprising a nucleic acid comprising at least a portion of an HLA-DRB1 allele, optionally flanked by nucleic acid sequences homologous to the nucleic acid sequences upstream and downstream of the double stranded break in the DRB1 gene, and wherein the resultant modified DRB1 gene, upon expression, confers resistance to the development of RA in the subject or a reduction of RA progression in the subject, comparable to a subject expressing the DRB1*04:02 allele. The subject to whom the modified cell(s) are administered may have no antibodies that recognize the human major histocompatibility complex, class II, DR4 protein or protein complex, as detected by ELISA or Bethesda assays.

Definitions

The terms "nucleic acid," "polynucleotide," and "oligonucleotide" are used interchangeably and refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T.

The terms "polypeptide," "peptide," and "protein" are used interchangeably to refer to a polymer of amino acid residues. The term also applies to amino acid polymers in which one or more amino acids are chemical analogues or modified derivatives of a corresponding naturally-occurring amino acids. As used throughout, by subject is meant an individual. Preferably, the subject is a mammal such as a primate, and, more preferably, a human. Non-human primates are subjects as well. The term subject includes domesticated animals, such as cats, dogs, etc., livestock (for example, cattle, horses, pigs, sheep, goats, etc.) and laboratory animals (for example, ferret, chinchilla, mouse, rabbit, rat, gerbil, guinea pig, etc.). Thus, veterinary uses and medical formulations are contemplated herein.

The term "at least a portion of an HLA-DRB1 allele" refers to a nucleotide sequence that contains less than the full length DRB1 allele. The portion of the DRB1 nucleotide may include the sequence encoding codon 71 of the DRB1*04:01 allele. The portion may be centered around the sequence encoding codon 71 of the DRB1*04:01 allele. In another aspect, the present invention provides a method for treating or preventing a disorder associated with expression of a polynucleotide sequence in a subject.

As described in greater detail herein, the present invention provides methods for treating or preventing RA in a subject. The terms "treat", "treating", "treatment", etc., as applied to a cell, include subjecting the cell to any kind of process or condition or performing any kind of manipulation or procedure on the cell. As applied to a subject, the terms refer to providing a cell in which a target polynucleotide sequence has been modified ex vivo according to the methods described herein to an individual. The subject is usually ill or injured, or at increased risk of becoming ill relative to an average member of the population and in need of such attention, care, or management. For example, the subject may be suffering from RA, or at increased risk of developing RA relative to an average member of the population and in need of such attention, care, or management.

As used herein, the term "treating" and "treatment" refers to administering to a subject an effective amount of cells with target polynucleotide sequences modified ex vivo according to the methods described herein so that the subject has a reduction in at least one symptom of the disease or an improvement in the disease (e.g., RA), for example, beneficial or desired clinical results. For purposes of this invention, beneficial or desired clinical results include, but are not limited to, alleviation of one or more symptoms, diminishment of extent of disease, stabilized (i.e., not worsening) state of disease, delay or slowing of disease progression, amelioration or palliation of the disease state, and remission (whether partial or total), whether detectable or undetectable. Treating can refer to prolonging survival as compared to expected survival if not receiving treatment. Thus, one of skill in the art realizes that a treatment may improve the disease condition, but may not be a complete cure for the disease. As used herein, the term "treatment" includes prophylaxis. Alternatively, treatment is "effective" if the progression of a disease is reduced or halted. "Treatment" can also mean prolonging survival as compared to expected survival if not receiving treatment. Those in need of treatment include those already diagnosed with a disorder associated with expression of a polynucleotide sequence, as well as those likely to develop such a disorder due to genetic susceptibility or other factors.

By "treatment," "prevention" or "amelioration" of a disease or disorder is meant delaying or preventing the onset of such a disease or disorder (e.g., RA), reversing, alleviating, ameliorating, inhibiting, slowing down or stopping the progression, aggravation or deterioration the progression or severity of a condition associated with such a disease or disorder. In one embodiment, the symptoms of a disease or disorder are alleviated by at least 5%, at least 10%, at least 20%, at least 30%, at least 40%, or at least 50%.

An exemplary method for treating or preventing a disorder associated with expression of a polynucleotide sequence in a subject comprises altering a target polynucleotide sequence in a cell ex vivo by contacting the polynucleotide sequence with a nuclease (e.g., a clustered regularly interspaced short palindromic repeats-associated (Cas) protein) and from one to two ribonucleic acids, wherein the ribonucleic acids direct the nuclease to, and hybridize to, a target motif of the target polynucleotide sequence, wherein the target polynucleotide sequence is cleaved, and modified, and introducing the modified cell into the subject, thereby treating or preventing a disorder associated with expression of the polynucleotide sequence.

HLA-DRB1 Gene Modifications

DRB1 molecules are highly polymorphic, and DRB1*04:01 is the gene associated with susceptibility to rheumatoid arthritis. In contrast, DRB1*04:02 is resistant to rheumatoid arthritis. The inventors have identified a single amino acid residue at position 71 that accounts for the difference in RA susceptibility between these two alleles. This single point mutation will alter the lysine at position 71 to glutamic acid (DRB1*01:$01^{K71E}$). Thus, in one aspect, the present invention is directed to the targeting and modification of DRB1*04:01 alleles in a subject suffering from RA using the methods described herein. Several DR4 alleles, notably DRB1*04:01, *04:04, and *04:05, are strongly associated with RA, while DRB1*04:02 is not. In addition, DRB1*01:01, *01:02, *10:01, and *14:02 have sometimes been associated with RA, particularly in non-Europeans. These disparate alleles have been hypothesized to contribute to RA via the presence of a "shared epitope," a common set of amino acids at positions 70-74 of the peptide-binding groove.

Identification of an RA subject's DR4 allele type can be readily made using techniques known in the art. For example, DNA from the subject can be extracted from leukocytes in whole blood and the endogenous coding regions can be analyzed by restriction analysis, direct DNA sequence analysis, Denaturing Gradient Gel Electrophoresis (DGGE), Chemical Mismatch Cleavage (CMC), and Denaturing High Performance Liquid Chromatography (DHPLC).

The gene modification targeted for repair by these methods of this disclosure may be a single nucleotide modification (i.e., a point mutation or SNP). The modification may be a modification of the codon encoding amino acid 71 of the DRB1*04:01 allele. The modification may be a modification that changes the codon encoding amino acid 71 of the DRB1*04:01 allele from a lysine to a glutamic acid.

Targeting Nucleases

In the methods of targeting and modifying a DRB1*04:01 allele of this disclosure, the DRB1*04:01 allele may be directly targeted by nucleases for modification. In the methods and compositions of this disclosure, the one or more nucleic acids encoding a nuclease that targets a DRB1*04:01 allele for modification, for example at codon 71, may be a CRISPR (Clustered Regularly Interspaced Short Palindromic Repeats)-associated (Cas) nuclease, or a transcription activator-like effector nuclease (TALEN), or a zinc finger nuclease (ZFN). Preferably, the encoded nuclease is a Cas9 nuclease.

Clustered Regularly Interspaced Short Palindromic Repeats (CRISPR) and CRISPR Associated (Cas) Nucleases is a system for genome editing that uses a short RNA to guide a nuclease to the DNA target. This system is called the CRISPR technology. (Mali P, Yang L, Esvelt K M, Aach J, Guell M, DiCarlo J E, Norville J E, Church G M. RNA-guided human genome engineering via Cas9. Science. 2013 Feb. 15; 339(6121):823-6; Gasiunas G, Barrangou R, Horvath P, Siksnys V. Cas9-crRNA ribonucleoprotein complex mediates specific DNA cleavage for adaptive immunity in bacteria. Proc Natl Acad Sci USA. 2012 Sep. 25; 109(39): E2579-86. Epub 2012 Sep. 4). The Clustered Regularly Interspaced Short Palindromic Repeats (CRISPR) and CRISPR Associated (Cas) system was discovered in bacteria and functions as a defense against foreign DNA, either viral or plasmid. In bacteria, the endogenous CRISPR/Cas system targets foreign DNA with a short, complementary single-stranded RNA (CRISPR RNA or crRNA) that localizes the Cas9 nuclease to the target DNA sequence. The DNA target sequence can be on a plasmid or integrated into the bacterial genome. The crRNA can bind on either strand of DNA and the Cas9 cleaves both strands (double strand break, DSB). An in vitro reconstitution of the *Streptococcus pyogenes* type II CRISPR system demonstrated that crRNA fused to a normally trans-encoded tracrRNA is sufficient to direct Cas9 protein to sequence-specifically cleave target DNA sequences matching the crRNA. The fully defined nature of this two-component system allows it to function in the cells of eukaryotic organisms such as yeast, plants, and mammals. By cleaving genomic sequences targeted by RNA sequences, such a system greatly enhances the ease of genome engineering. The Cas9 molecule may be a Cas9 polypeptide. The Cas9 polypeptide may be a *Staphylococcus aureus* Cas9 polypeptide. The Cas9 polypeptide may be a *Streptococcus pyogenes* Cas9 polypeptide. The Cas9 polypeptide may be a human codon optimized Cas9 polypeptide. The guide RNA molecule and the Cas9 polypeptide may be associated in a pre-formed ribonucleotide complex.

The crRNA targeting sequences are transcribed from DNA sequences known as protospacers. Protospacers are clustered in the bacterial genome in a group called a CRISPR array. The protospacers are short sequences (approx. 20 bp) of known foreign DNA separated by a short palindromic repeat and kept like a record against future encounters. To create the CRISPR targeting RNA (crRNA), the array is transcribed and the RNA is processed to separate the individual recognition sequences between the repeats. In the Type II system, the processing of the CRISPR array transcript (pre-crRNA) into individual crRNAs is dependent on the presence of a trans-activating crRNA (tracrRNA) that has sequence complementary to the palindromic repeat. When the tracrRNA hybridizes to the short palindromic repeat, it triggers processing by the bacterial double-stranded RNA-specific ribonuclease, RNase III. Any crRNA and the tracrRNA can then both bind to the Cas9 nuclease, which then becomes activated and specific to the DNA sequence complimentary to the crRNA. (Mali P, Science. 2013 supra; Gasiunas G, Proc Natl Acad Sci USA. 2012 supra). Thus, this disclosure includes an isolated crRNA that contains an HLA-DRB1-specific protospacer domain of about 17 nucleotides to about 20 nucleotides. These isolated crRNAs may comprise the nucleotide sequence: GGAC-CUCGUCUUCGCCCGGCGCC (SEQ ID NO:1).

Zinc Finger Nucleases (ZFNs) are engineered nucleases that have emerged as powerful tools for site-specific editing of the genome. For example, zinc finger nucleases (ZFNs) are hybrid proteins containing the zinc-finger DNA-binding domain present in transcription factors and the non-specific cleavage domain of the endonuclease Foki. (Li et al., In vivo genome editing restores haemostasis in a mouse model of haemophilia, Nature 2011 Jun. 26; 475(7355):217-21).

The same sequences targeted by the CRISPR approach, discussed above, can also be targeted by the zinc finger nuclease approach for genome editing. Zinc finger nucleases (ZFNs) are a class of engineered DNA-binding proteins that facilitate targeted editing of the genome by creating double-strand breaks in DNA at user-specified locations. Each Zinc Finger Nuclease (ZFN) consists of two functional domains: 1) a DNA-binding domain comprised of a chain of two-finger modules, each recognizing a unique hexamer (6 bp) sequence of DNA, wherein two-finger modules are stitched together to form a Zinc Finger Protein, each with specificity of ≥24 bp; and 2) a DNA-cleaving domain comprised of the nuclease domain of Fok I. The DNA-binding and DNA-cleaving domains are fused together and recognize the targeted genomic sequences, allowing the Foki domains to form a heterodimeric enzyme that cleaves the DNA by creating double stranded breaks. Zinc finger nucleases can be readily made using techniques known in the art (Wright D A, et al. Standardized reagents and protocols for engineering zinc finger nucleases by modular assembly. Nat Protoc. 2006; 1(3):1637-52). Engineered zinc finger nucleases can stimulate gene targeting at specific genomic loci in animal and human cells. The construction of artificial zinc finger arrays using modular assembly has been described. The archive of plasmids encoding more than 140 well-characterized zinc finger modules together with complementary web-based software for identifying potential zinc finger target sites in a gene of interest has also been described. These reagents enable easy mixing-and-matching of modules and transfer of assembled arrays to expression vectors without the need for specialized knowledge of zinc finger sequences or complicated oligonucleotide design (Wright D A, Nat Protoc. 2006, supra). Any gene in any organism can be targeted with a properly designed pair of ZFNs. Zinc-finger recognition depends only on a match to the target DNA sequence (Carroll, D. Genome engineering with zinc-finger nucleases. Genetics Society of America, 2011, 188(4), pp 773-782).

Transcription Activator-Like Effector Nucleases (TALENs) are emerging as a preferred alternative to zinc finger nucleases (ZFNs) for certain types of genome editing. The C-terminus of the TALEN component carries nuclear localization signals (NLSs), allowing import of the protein to the nucleus. Downstream of the NLSs, an acidic activation domain (AD) is also present, which is probably involved in the recruitment of the host transcriptional machinery. The central region harbors a series of nearly identical 34/35 amino acids modules repeated in tandem. Residues in positions 12 and 13 are highly variable and are referred to as repeat-variable di-residues (RVDs). Each RVD in a repeat of a particular TALE determines the interaction with a single nucleotide. Most of the variation between TALEs relies on the number (ranging from 5.5 to 33.5) and/or the order of the quasi-identical repeats. Estimates using design criteria derived from the features of naturally occurring TALEs suggest that, on average, a suitable TALEN target site may be found every 35 base pairs in genomic DNA. Compared with ZFNs, the cloning process of TALENs is easier, the specificity of recognized target sequences is higher, and off-target effects are lower. In one study, TALENs designed to target CCR5 were shown to have very little activity at the highly homologous CCR2 locus, as compared with CCR5-specific ZFNs that had similar activity at the two sites.

Following the introduction of the nuclease and the guide RNA into the cell, the nuclease catalyzes a double stranded break in the DNA between their binding sites. If a double stranded break occurs in the presence of, for example, a template plasmid (DP), which contains a stretch of DNA with a left homology (HL) and right homology (HR) arm that have identical DNA sequences to that in the native chromosomal DNA 5' and 3' of the region flanking the break-point, homologous recombination occurs very efficiently. Accordingly, the present invention includes the introduction of a nucleic acid sequence that serves as a template sequence during homologous recombination which includes a portion of the DRB1*04:02 allele that replaces, and thus modifies, a portion of the subject's DRB1 gene, including, specifically, the portion encoding codon 71.

The guide RNA is an RNA that includes targeting sequence complementary to genomic DNA of the cell, preferably a DRB1 gene sequence in the cell, that may specifically include a DRB1*04:01 allele sequence in the cell. The guide RNA may include between about 10 to about 250 nucleotides, or between about 20 to about 100 nucleotides. The guide RNA may include the nucleotide sequence: GGACCUCGUCUUCGCCCGGCGCC (SEQ ID NO:1).

The guide RNA may include one or more chemically-modified nucleotides having a modification selected from a group consisting of a ribose modification, an end-modifying group, and an internucleotide modifying linkage. The guide RNA may include a ribonucleic acid containing at least one modified nucleotide selected from the group consisting of pseudouridine, 5-methylcytodine, 2-thio-uridine, 5-methyluridine-5'-triphosphate, 4-thiouridine-5'-triphosphate, 5,6-dihydrouridine-5'-triphosphate, and 5-azauridine-5'-triphosphate.

Within type II CRISPR systems, short guiding CRISPR RNAs (crRNAs) consisting of "spacer" units, direct cleavage of DNA complementary to the spacer sequence. Within bacteria, the Type II effector system consists of a long pre-crRNA transcribed from the spacer-containing CRISPR locus, the multifunctional Cas9 protein, and a tracrRNA important for gRNA processing. The tracrRNAs hybridize to the repeat regions separating the spacers of the pre-crRNA, initiating dsRNA cleavage by endogenous RNase III, which is followed by a second cleavage event within each spacer by Cas9, producing mature crRNAs that remain associated with the tracrRNA and Cas9. The nuclease enzyme used in the methods of the present disclosure (such as Cas9) unwinds the DNA duplex and searches for sequences matching the crRNA to cleave. Target recognition occurs upon detection of complementarity between a "protospacer" sequence in the target DNA and the remaining spacer sequence in the crRNA. Importantly, Cas9 cuts the DNA only if a correct protospacer-adjacent motif (PAM) is also present at the 3' end. According to certain aspects, a different protospacer-adjacent motif can be utilized. For example, the S. pyogenes system requires an NGG sequence, where N can be any nucleotide. S. thermophilus Type II systems require NGGNG, and NNAGAAW, respectively, while different S. mutans systems tolerate NGG or NAAR. Bioinformatic analyses have generated extensive databases of CRISPR loci in a variety of bacteria that may serve to identify additional useful PAMs and expand the set of CRISPR-targetable sequences. In S. thermophilus, Cas9 generates a blunt-ended double-stranded break 3 bp prior to the 3' end of the protospacer, a process mediated by two catalytic domains in the Cas9 protein: an HNH domain that cleaves the complementary strand of the DNA and a RuvC-like domain that cleaves the non-complementary strand. While the S. pyogenes system has not been characterized to the same level of precision, DSB formation also occurs towards the 3' end of the protospacer. If one of the two nuclease domains is inactivated, Cas9 will function as a nickase in vitro and in human cells in vivo.

Therefore, the guide RNA used in the methods of this disclosure may be a crRNA-tracrRNA fusion. In these methods, crRNA-tracrRNA fusion transcripts are expressed from a promoter (such as the human U6 polymerase III promoter). Such guide RNAs may be directly transcribed by the cell. This aspect advantageously avoids reconstituting the RNA processing machinery employed by bacterial CRISPR systems. In these methods, the crRNA may comprise the nucleotide sequence: GGACCUCGUC-UUCGCCCGGCGCC (SEQ ID NO:1).

The nuclease protein (e.g., Cas9 protein) may be combined with a gRNA molecule to form a ribonucleoprotein (RNP) complex to be administered to the subject or delivered into the cell. Direct delivery of a nuclease-gRNA RNP complex to cells eliminates the needs of expression from nucleic acid (e.g., transfection of plasmids encoding the nuclease and gRNA). It also eliminates unwanted integration of DNA segments derived from nucleic acid delivery (e.g., transfection of plasmids encoding the nuclease and gRNA). Therefore, this RNP complex provides an alternative delivery approach for use in the methods of this disclosure, which provides rapid action, fast turnover, high rate of on-target modification, reduced off target effects, and less toxicity to cells. It can also be utilized to deliver the nuclease/gRNA complex to hard to transfect cells (e.g., hard to transfect primary and pluripotent stem cells). A nuclease/gRNA ribonucleoprotein (RNP) complex usually is formed prior to administration (i.e., pre-formed). When multiple (more than one) nuclease/gRNA ribonucleoprotein (RNP) complexes are involved, they can be delivered (or administered) simultaneously or sequentially. The nuclease/gRNA ribonucleoprotein (RNP) complexes may be delivered to cells by electroporation.

Alternatively or additionally, the nuclease molecule is introduced into the cell as a nucleic acid encoding a nuclease protein (e.g., a Cas9 protein). Similarly, the guide RNA may be introduced into the cell as a nucleic acid encoding the guide RNA. Similarly, the nuclease protein may be introduced into the cell as a nucleic acid encoding the nuclease protein, and the cell expresses the guide RNA and the nuclease protein. The nuclease protein (as well as the guide RNA and/or the template nucleic acid) may be introduced into the cell within an adeno-associated virus (AAV) or an integration deficiency lentivirus.

Template Nucleic Acid Sequence

A "template nucleic acid" refers to a nucleic acid sequence which can be used in conjunction with the nuclease (e.g., a Cas9 molecule) and a guide RNA molecule to alter the structure of the targeted nucleic acid (e.g., DRB1 genomic DNA). The targeted nucleic acid is modified to have some or all of the sequence of the template nucleic acid, typically at or near cleavage site(s). The template nucleic acid may be single stranded or double stranded. The template nucleic acid may be DNA (e.g., double stranded DNA), or single stranded DNA, or RNA (e.g., double stranded RNA or single stranded RNA). The template nucleic acid may be encoded on the same vector backbone (e.g., AAV genome, plasmid DNA) as the nuclease and/or the guide RNA, and the template nucleic acid may be excised from a vector backbone in vivo (e.g., it is flanked by guide RNA recognition sequences). The template DNA may be encoded in an ILDV. The template nucleic acid may be an exogenous nucleic acid sequence. The template nucleic acid sequence may be an endogenous nucleic acid sequence (e.g., an endogenous homologous region). The template nucleic acid may be a single stranded oligonucleotide corresponding to a plus strand or a minus strand of a nucleic acid sequence.

The donor or "template" nucleic acid sequence comprises a nucleic acid encoding a portion of the DRB1*04:02 allele. The template sequence may be flanked on each side by regions of nucleic acid which are homologous to the DRB1*04 gene. Each of these homologous regions may include about 20, 50, 75, 100, 200, 300, 400, 500, 600, 700, 800, 900, 1000 or more nucleotides homologous with the subject's DRB1 gene. Each of the homologous regions flanking the template sequence may be between about 200 to about 1,200 nucleotides, between 400 and about 1000 nucleotides, or between about 600 and about 900 nucleotides. In one embodiment, each homologous region is between about 800 and about 900 nucleotides. Thus, each template nucleic acid sequence may include a sequence that replaces or modifies the subject's endogenous DRB1*04:01 allele, and 5' and 3' flanking sequences which are homologous to portions of the DRB1 gene.

The template sequence is derived based on the specific nucleotide, or codon, or portion, or region within the subject's DRB1 gene that is targeted for replacement or modification. Accordingly, the length of the template sequence can vary. For example, when repairing a point mutation, such as a change in the sequence encoding codon 71 in the DRB104 allele, the template sequence may include only a small number of replacement nucleotide sequences compared with, for example, a template sequence designed for replacing or repairing a larger portion or region of the DRB1 gene, such as an inversion. Therefore, a template sequence may be of any length, for example between 2 and 10,000 nucleotides in length (or any integer value there between or there above), preferably between about 100 and 1,000 nucleotides in length (or any integer there between), more preferably between about 200 and 500 nucleotides in length. The designing of template sequence nucleic acids is known in the art (for example, see Cermak et al., Efficient design and assembly of custom TALEN and other TAL effector-based constructs for DNA targeting, Nucleic Acid Res. 2011 Sep. 1; 39 (17):7879). In exemplary methods of this disclosure, the template sequence includes the nucleotide sequence of codon 71 of the DRB1*04:02 allele.

In the methods of this disclosure, the gene sequence targeted for modification is a single nucleotide polymorphism (SNP), and the template sequence includes a nucleic acid sequence that modifies or replaces the SNP with a sequence that is considered the "wild-type" gene sequence or a different allelic variation at that same site, for example, the DRB1*04:02 allele sequence at that same site. In related methods of this disclosure, the gene sequence targeted for modification includes a deletion and the template sequence, or includes a nucleic acid sequence that replaces the deletion with a sequence that does not include the deletion, for example, the wild-type DRB1 sequence, or the DRB1*04:02 allele sequence.

In related methods of this disclosure, the gene sequence targeted for modification is an insertion, and the target sequence includes a nucleic acid sequence that encodes a portion of the DRB1 gene that removes the insertion and provides for the production of a functional DRB1 gene product.

In these methods of this disclosure, the template sequence may contain sequences that are homologous, but not identical (for example, contain nucleic acid sequence encoding wild-type amino acids or differing ns-SNP amino acids), to genomic sequences in the region of interest, thereby stimulating homologous recombination to insert a non-identical sequence in the region of interest. Thus, portions of the template sequence that are homologous to sequences in the region of interest may exhibit between about 80 to about 99% sequence identity to the genomic sequence that is replaced. The homology between the template and genomic sequence is higher than 99%, for example if only 1 nucleotide differs between the template and genomic sequences of over 100 contiguous base pairs. A non-homologous portion of the template sequence may contain sequences not present in the region of interest, such that new sequences are introduced into the region of interest. In these instances, the non-homologous sequence is generally flanked by sequences of between 50 and 1,000 base pairs, or any number of base pairs greater than 1,000, that are homologous or identical to sequences in the region of interest. In other embodiments, the template sequence is non-homologous to the first sequence, and is inserted into the genome by non-homologous recombination mechanisms.

The template nucleic acid may be a single stranded oligodeoxynucleotide (ssODN). The ssODN may comprise a 5' phosphorothioate modification. The ssODN may comprise a 3' phosphorothioate modification. The ssODN may comprise a 5' phosphorothioate modification and a 3' phosphorothioate modification.

The template nucleic acids for modifying the DRB1 gene may be designed for use as a single-stranded oligonucleotide (e.g., a single-stranded oligodeoxynucleotide (ssODN)). When using a ssODN, 5' and 3' homology arms may range up to about 200 base pairs (bp) in length, e.g., at least 25, 50, 75, 100, 125, 150, 175, or 200 bp in length. Longer homology arms are also contemplated for ssODNs as improvements in oligonucleotide synthesis continue to be made. A longer homology arm may be made by a method other than chemical synthesis, e.g., by denaturing a long double stranded nucleic acid and purifying one of the strands, e.g., by affinity for a strand-specific sequence anchored to a solid substrate.

Targeted Cells

The gene targeting and modification techniques using the different nucleases described above can be carried out using many different target cells. For example, the transduced cells may include endothelial cells, hepatocytes, or stem cells. In one embodiment, the cells can be targeted in vivo. In one embodiment, the cells can be targeted using ex vivo approaches and reintroduced into the subject.

The target cells from the subject may be endothelial cells, such as blood outgrowth endothelial cells (BOECs). Characteristics that render BOECs attractive for gene modification and delivery include the: (i) ability to be expanded from progenitor cells isolated from blood, (ii) mature endothelial cell, stable, phenotype and normal senescence (about 65 divisions), (iii) prolific expansion from a single blood sample to a thousand or more BOECs, (iv) resilience, which unlike other endothelial cells, permits cryopreservation and hence multiple doses for a single patient prepared from a single isolation. Methods of isolation of BOECs are known, where the culture of peripheral blood provides a rich supply of autologous, highly proliferative endothelial cells, also referred to as blood outgrowth endothelial cells (Bodempudi V, et al., Blood outgrowth endothelial cell-based systemic delivery of antiangiogenic gene therapy for solid tumors. Cancer Gene Ther. 2010 December; 17(12):855-63).

Studies in animal models have revealed properties of blood outgrowth endothelial cells that indicate that they are suitable for use in ex vivo gene modification strategies. For example, a key finding concerning the behavior of canine blood outgrowth endothelial cells (cBOECs) is that cBOECs persist and expand within the canine liver after infusion (Milbauer L C, et al. Blood outgrowth endothelial cell migration and trapping in vivo: a window into gene therapy. 2009 April; 153(4):179-89). Whole blood clotting time (WBCT) in the HA model was also improved after administration of engineered cBOECs. WBCT dropped from a pretreatment value of under 60 min to below 40 min and sometimes below 30 min.

In these methods, the target cells from the subject are eukaryotic cells that may be stem cells, and specifically hematopoietic stem cells (HSCs), as hematopoietic cells likely represent the main cell source of DRB1 gene products that present modified peptides and trigger RA.

The cell (or population of cells) may be a primary blood cell, or population of primary blood cells. The cell or population of cells may be a bone marrow cell, a peripheral blood cell, or a cell generated from an induced pluripotent stem (iPS) cell, an embryonic stem (ES) cell, an endothelial cell, a myeloid progenitor cell, a circulating blood cell, a mobilized blood cell, a multipotent progenitor cell, and a lineage restricted progenitor cell, or a population of any of these cells. The population of cells may be a heterogeneous population of cells or a homogeneous population of cells.

The stem cells may be induced pluripotent stem cells (iPSCs). Induced pluripotent stem cells (iPSCs) are a type of pluripotent stem cell artificially derived from a non-pluripotent cell, typically an adult somatic cell, by inducing expression of specific genes and factors important for maintaining the defining properties of embryonic stem cells. Induced pluripotent stem cells (iPSCs) have been shown in several examples to be capable of site specific gene targeting by nucleases (Ru, R. et al. Targeted genome engineering in human induced pluripotent stem cells by penetrating TALENs. Cell Regeneration. 2013, 2:5; Sun N, Zhao H. Seamless correction of the sickle cell disease mutation of the HBB gene in human induced pluripotent stem cells using TALENs. Biotechnol Bioeng. 2013 Aug. 8). Induced pluripotent stem cells (iPSCs) can be isolated using methods known in the art (see, for example, Lorenzo, I M. Generation of Mouse and Human Induced Pluripotent Stem Cells (iPSC) from Primary Somatic Cells. Stem Cell Rev. 2013 August; 9(4): 435-50).

In some instances, pure populations of some cell types may not promote sufficient homing and implantation upon reintroduction of the transduced cells into the subject, to provide extended and sufficient expression of the modified DRB1 gene. Therefore, some cell types may be co-cultured with different cell types to help promote cell properties (i.e. ability of cells to engraft in the bone marrow).

Cell Delivery

Methods of nucleic acid delivery are well known in the art (see, e.g., PCT publication No. WO 2012/051343). In the methods of this disclosure, the described nuclease encoding nucleic acids can be introduced into the cell as DNA or RNA, single-stranded or double-stranded and can be introduced into a cell in linear or circular form. In one embodiment, the nucleic acids encoding the nuclease are introduced into the cell as mRNA. The template sequence can be introduced into the cell as single-stranded or double-stranded DNA and can be introduced into a cell in linear or circular form. If introduced in linear form, the ends of the nucleic acids can be protected (e.g., from exonucleolytic degradation) by methods known to those of skill in the art. For example, one or more dideoxynucleotide residues are added to the 3' terminus of a linear molecule and/or self-complementary oligonucleotides are ligated to one or both ends (see, for example, Chang et al. (1987) Proc. Natl. Acad. Sci. USA 84:4959-4963; Nehls et al. (1996) Science 272: 886-889). Additional methods for protecting exogenous polynucleotides from degradation include, but are not limited to, addition of terminal amino group(s) and the use of modified internucleotide linkages, such as phosphorothioates, phosphoramidates, and O-methyl ribose or deoxyribose residues.

The nucleic acids may be introduced into a cell as part of a vector molecule having additional sequences, such as replication origins, promoters and genes encoding antibiotic resistance. Moreover, the nucleic acids can be introduced as naked nucleic acid, as nucleic acid complexed with an agent such as a liposome or poloxamer, or can be delivered by viruses (e.g., adenovirus, AAV, herpesvirus, retrovirus, lentivirus). Thus, this disclosure includes vectors that may encode one or more of the nuclease (e.g., Cas9 nuclease), guide RNA (which may be encoded as a tracrRNA-crRNA fusion), and a template nucleic acid. The vector may be an adenovirus vector, an integration-deficient lentiviral vector (IDLV), or an integration-deficient foamyviral vector (IDFV).

The nucleic acids may be delivered in vivo or ex vivo by any suitable means. Methods of delivering nucleic acids are described, for example, in U.S. Pat. Nos. 6,453,242; 6,503, 717; 6,534,261; 6,599,692; 6,607,882; 6,689,558; 6,824, 978; 6,933,113; 6,979,539; 7,013,219; and 7,163,824, each of which is incorporated herein by this reference.

Any vector systems may be used including, but not limited to, plasmid vectors, retroviral vectors, lentiviral vectors, adenovirus vectors, poxvirus vectors; herpesvirus vectors and adeno-associated virus vectors, etc. (see, for example, U.S. Pat. Nos. 6,534,261; 6,607,882; 6,824,978; 6,933,113; 6,979,539; 7,013,219; and 7,163,824). Furthermore, any of these vectors may comprise one or more of the sequences needed for treatment of RA. Thus, when one or more nucleic acids are introduced into the cell, the nucleases and/or template sequence nucleic acids may be carried on the same vector or on different vectors. When multiple vectors are used, each vector can comprise a sequence encoding a nuclease, or a template nucleic acid sequence. Alternatively, two or more of the nucleic acids can be contained on a single vector.

Conventional viral and non-viral based gene transfer methods can be used to introduce nucleic acids encoding the nuclease in cells (e.g., mammalian cells) and target tissues. Non-viral vector delivery systems include DNA plasmids, naked nucleic acid, and nucleic acid complexed with a delivery vehicle such as a liposome or poloxamer. Viral vector delivery systems include DNA and RNA viruses, which have either episomal or integrated genomes after delivery to the cell. Methods of non-viral delivery of nucleic acids include sonoporation, electroporation, lipofection, microinjection, biolistics, virosomes, liposomes, immunoliposomes, polycation or lipid:nucleic acid conjugates, naked DNA, artificial virions, and agent-enhanced uptake of DNA.

Additional exemplary nucleic acid delivery systems include those provided by Amaxa Biosystems (Cologne, Germany), Maxcyte, Inc. (Rockville, Md.), BTX Molecular Delivery Systems (Holliston, Mass.) and Copernicus Therapeutics Inc, (see for example, U.S. Pat. No. 6,008,336). Lipofection is described in e.g., U.S. Pat. Nos. 5,049,386; 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those described in PCT publication Nos. WO 91/17424 and WO 91/16024.

The preparation of lipid:nucleic acid complexes, including targeted liposomes such as immunolipid complexes, is well known to those of skill in the art (see, e.g., Crystal, Science 270:404-410 (1995); Blaese et al, Cancer Gene Ther. 2:291-297 (1995); Behr et al, Bioconjugate Chem. 5:382-389 (1994); Remy et al, Bioconjugate Chem. 5:647-654 (1994); Gao et al, Gene Therapy 2:710-722 (1995); Ahmad et al, Cancer Res. 52:4817-4820 (1992); U.S. Pat. Nos. 4,186,183, 4,217,344, 4,235,871, 4,261,975, 4,485,054, 4,501,728, 4,774,085, 4,837,028, and 4,946,787).

Additional methods of delivery include the use of packaging the nucleic acids to be delivered into EnGeneIC delivery vehicles (EDVs). These EDVs are specifically delivered to target tissues using bispecific antibodies where one arm of the antibody has specificity for the target tissue and the other has specificity for the EDV. The antibody brings the EDVs to the target cell surface and then the EDV is brought into the cell by endocytosis. Once in the cell, the contents are released (see MacDiarmid et al (2009) Nature Biotechnology 27(7):643).

The use of RNA or DNA viral based systems for the delivery of nucleic acids take advantage of highly evolved processes for targeting a virus to specific cells in the body and trafficking the viral payload to the nucleus. Viral vectors can be administered directly to patients (in vivo) or they can be used to treat cells in vitro and the modified cells are administered to patients (ex vivo). Conventional viral based systems for the delivery of nucleic acids include, but are not limited to, retroviral, lentivirus, adenoviral, adeno-associated, vaccinia and herpes simplex virus vectors for gene transfer.

The tropism of a retrovirus can be altered by incorporating foreign envelope proteins, expanding the potential population of target cells. Lentiviral vectors are retroviral vectors that can transduce or infect non-dividing cells and typically produce high viral titers. Selection of a retroviral gene transfer system depends on the target tissue. Retroviral vectors are comprised of cz's-acting long terminal repeats with packaging capacity for up to 6-10 kb of foreign sequence. The minimum cz's-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immunodeficiency virus (SIV), human immunodeficiency virus (HIV), and combinations thereof (see, e.g., Buchscher et al, J. Virol. 66:2731-2739 (1992); Johann et al, J. Virol. 66:1635-1640 (1992); Sommerfelt et al., Virol. 176:58-59 (1990); Wilson et al, J. Virol. 63:2374-2378 (1989); Miller et al, J. Virol. 65:2220-2224 (1991); PCT US94/05700).

In applications in which transient expression is preferred, adenoviral based systems can be used. Adenoviral based vectors are capable of very high transduction efficiency in many cell types and do not require cell division. With such vectors, high titer and high levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures (see, e.g., West et al, Virology 160:38-47 (1987); U.S. Pat. No. 4,797,368; WO 93/24641; Kotin, Human Gene Therapy 5:793-801 (1994); Muzyczka, J. Clin. Invest. 94:1351 (1994). Construction of recombinant AAV vectors is described in a number of publications, including U.S. Pat. No. 5,173,414; Tratschin et al, Mol Cell. Biol. 5:3251-3260 (1985); Tratschin, et al, Mol. Cell. Biol. 4:2072-2081 (1984); Hermonat & Muzyczka, PNAS 81:6466-6470 (1984); and Samulski et al, J. Virol. 63:03822-3828 (1989).

A variety of viral vector approaches are currently available for gene transfer in clinical trials, which utilize approaches that involve complementation of defective vectors by genes inserted into helper cell lines to generate the transducing agent. pLASN and MFG-S are examples of retroviral vectors that have been used in clinical trials (Dunbar et al, Blood 85:3048-305 (1995); Kohn et al, Nat. Med. 1:1017-102 (1995); Malech et al, PNAS 94:22 12133-12138 (1997)). PA317/pLASN was the first therapeutic vector used in a gene therapy trial. (Blaese et al, Science 270:475-480 (1995)). Transduction efficiencies of 50% or greater have been observed for MFG-S packaged vectors. (Ellem et al, Immunol Immunother. 44(1):10-20 (1997); Dranoff et al, Hum. Gene Ther. 1:111-2 (1997). Recombinant adeno-associated virus vectors (rAAV) are an alternative gene delivery systems based on the defective and nonpathogenic parvovirus adeno-associated type 2 virus. All vectors are derived from a plasmid that retains only the AAV 145 bp inverted terminal repeats flanking the transgene expression cassette. Efficient gene transfer and stable transgene delivery due to integration into the genomes of the transduced cell are key features for this vector system. (Wagner et al, Lancet 351: 9117 1702-3 (1998), Kearns et al, Gene Ther. 9:748-55 (1996)). Other AAV serotypes, including AAV1, AAV2, AAV3, AAV4, AAV5, AAV6, AAV7, AAV8, AAV9 and AAVrh.10 and any novel AAV serotype may also be used in the methods of this disclosure.

Replication-deficient recombinant adenoviral vectors (Ad) can be produced at high titer and readily infect a number of different cell types. Most adenovirus vectors are engineered such that a transgene replaces the Ad EI a, EI b, and/or E3 genes; subsequently the replication defective vector is propagated in human 293 cells that supply deleted gene function in trans. Ad vectors can transduce multiple types of tissues in vivo, including non-dividing, differentiated cells such as those found in liver, kidney and muscle. Conventional Ad vectors have a large carrying capacity. An example of the use of an Ad vector in a clinical trial involved polynucleotide therapy for antitumor immunization with intramuscular injection (Sterman et al, Hum. Gene Ther. 7:1083-9 (1998)). Additional examples of the use of adenovirus vectors for gene transfer in clinical trials include Rosenecker et ah, Infection 24:1 5-10 (1996); Sterman et ah, Hum. Gene Ther. 9:7 1083-1089 (1998); Welsh et ah, Hum. Gene Ther. 2:205-18 (1995); Alvarez et al, Hum. Gene Ther. 5:597-613 (1997); Topf et al, Gene Ther. 5:507-513 (1998); Sterman et al, Hum. Gene Ther. 7:1083-1089 (1998).

Packaging cells are used to form virus particles that are capable of infecting a host cell. Such cells include 293 cells, which package adenovirus, and ψ2 cells or PA317 cells, which package retrovirus. Viral vectors used in gene therapy are usually generated by a producer cell line that packages a nucleic acid vector into a viral particle. The vectors typically contain the minimal viral sequences required for packaging and subsequent integration into a host (if applicable), other viral sequences being replaced by an expression cassette encoding the protein to be expressed. The missing viral functions are supplied in trans by the packaging cell line. For example, AAV vectors used in gene therapy typically only possess inverted terminal repeat (ITR) sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV.

A viral vector can be modified to have specificity for a given cell type by expressing a ligand as a fusion protein with a viral coat protein on the outer surface of the virus. The ligand is chosen to have affinity for a receptor known to be present on the cell type of interest (see, for example, Han et ah, Proc. Natl. Acad. Sci. USA 92:9747-9751 (1995), reporting that Moloney murine leukemia virus can be modified to express human heregulin fused to gp70, and the recombinant virus infects certain human breast cancer cells expressing human epidermal growth factor receptor). This can be used with other virus-target cell pairs, in which the target cell expresses a receptor and the virus expresses a fusion protein comprising a ligand for the cell-surface receptor. For example, filamentous phage can be engineered to display antibody fragments (e.g., FAB or Fv) having specific binding affinity for virtually any chosen cellular receptor. Although the above description applies primarily to viral vectors, the same principles can be applied to non-viral vectors. Such vectors can be engineered to contain specific uptake sequences which favor uptake by specific target cells.

Vectors can be delivered in vivo by administration to an individual patient, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual subject (e.g., lymphocytes, bone marrow aspirates, tissue biopsy) or universal donor hematopoietic stem cells, followed by re-implantation of the cells into the subject, usually after selection for cells which have incorporated the vector.

Vectors (e.g., retroviruses, adenoviruses, liposomes, etc.) containing the nucleic acids of this disclosure can also be administered directly to an organism for transduction of cells in vivo.

Alternatively, naked DNA can be administered. Administration may be by any of the routes normally used for introducing a molecule into ultimate contact with blood or tissue cells including, but not limited to, injection, infusion, topical application and electroporation. Suitable methods of administering such nucleic acids are available and well known to those of skill in the art, and, although more than one route can be used to administer a particular composition, a particular route can often provide a more immediate and more effective reaction than another route.

Vectors suitable for introduction of the nucleic acids of this disclosure include non-integrating lentivirus vectors (IDLV). See, for example, Ory et al. (1996) Proc. Natl. Acad. Sci. USA 93:11382-11388; Dull et al. (1998) J. Virol. 72:8463-8471; Zuffery et al. (1998) J. Virol. 72:9873-9880; Follenzi et al. (2000) Nature Genetics 25:217-222; U.S. Patent Publication No 2009/054985.

Administration can be by any means in which the polynucleotides are delivered to the desired target cells. For example, both in vivo and ex vivo methods are contemplated. In one embodiment, the nucleic acids are introduced into a subject's cells that have been explanted from the subject, and reintroduced following DRB1 gene modification.

For ex vivo methods, the modified cells are preferably autologous cells, i.e., a cell or cells taken from a subject who is in need of altering a DRB1 target polynucleotide sequence in the cell or cells (i.e., the donor and recipient are the same individual). Autologous cells have the advantage of avoiding any immunologically-based rejection of the cells. Alternatively, the cells can be heterologous, e.g., taken from a donor. The second subject can be of the same or different species. Typically, when the cells come from a donor, they will be from a donor who is sufficiently immunologically compatible with the recipient, i.e., will not be subject to transplant rejection, to lessen or remove the need for immunosuppression. In some embodiments, the cells are taken from a xenogeneic source, i.e., a non-human mammal that has been genetically engineered to be sufficiently immunologically compatible with the recipient, or the recipient's species. Methods for determining immunological compatibility are known in the art, and include tissue typing to assess donor-recipient compatibility for HLA and ABO determinants (see, e.g., Transplantation Immunology, Bach and Auchincloss, Eds. (Wiley, John & Sons, Incorporated 1994). Administration of modified autologous cells may advantageously be achieved by administering the population of modified cells to the subject as an autologous bone marrow transplant.

If ex vivo methods are employed, cells or tissues can be removed, expanded, and maintained outside the body according to standard protocols well known in the art. The compositions can be introduced into the cells via any gene transfer mechanism as described above, such as, for example, calcium phosphate mediated gene delivery, electroporation, microinjection, proteoliposomes, or viral vector delivery. The transduced cells can then be infused (e.g., in a pharmaceutically acceptable carrier) or homotopically transplanted back into the subject per standard methods for the cell or tissue type. Standard methods are known for transplantation or infusion of various cells into a subject.

In these methods, a DRB1*04:01 allele is identified in a cell from a subject having RA or at risk of developing RA, and the DRB1*04 allele is modified to resemble the DRB1*04:02 allele. For example, a BOEC or iPSC, is identified and modified using the nuclease approach described above and a template sequence that is identical to a portion of a DRB1*04:02 allele is substituted into the DRB1*04 allele in the cell. In one embodiment, the modification takes place ex vivo, as a cell, for example a BOEC or iPSC, is explanted from the subject, modified, and reintroduced into the subject as described above. Following modification, the cell is capable of producing the DRB1*04 gene product, including a glutamic acid residue at position 71. The expression of the DRB1*04 gene product in vivo leads to a reduction, delay, or inhibition in an undesired immune response specific to the DRB1 antigen or epitope, and reduction, amelioration, or suppression of RA in the subject. The reduced immune response can be the result of MHC Class II-restricted presentation and/or B cell presentation, or any other presentation leading to the minimized or reduced immunogenicity of the modified DRB1 gene product.

The reduction in the auto-immune response to the DRB1 gene product can be measured in vivo or may be measured in vitro. One of ordinary skill in the art is familiar with such in vivo or in vitro measurements. Immune responses can be monitored using, for example, methods of assessing immune cell number and/or function, tetramer analysis, ELISPOT, flow cytometry-based analysis of cytokine expression, cytokine secretion, cytokine expression profiling, gene expression profiling, protein expression profiling, analysis of cell surface markers, PCR-based detection of immune cell receptor gene usage (see T. Clay et al., "Assays for Monitoring Cellular Immune Response to Active Immunotherapy of Cancer" Clinical Cancer Research 7:1127-1135 (2001)), etc. Immune responses may also be monitored using, for example, methods of assessing protein levels in plasma or serum, immune cell proliferation and/or functional assays, etc. Tolerogenic immune responses may also be monitored by assessing the induction of FoxP3. The reduction of an undesired immune response may also be assessed by determining clinical endpoints, clinical efficacy, clinical symptoms, disease biomarkers and/or clinical scores. Tolerogenic immune responses can also be assessed with diagnostic tests to assess the presence or absence of inhibitors.

In these methods, cells from a subject can be harvested, modified, and then stored for future administration to the subject. The cells can be administered in effective amounts, such as the effective amounts described elsewhere herein. The amount of expressing cells present in the compositions or dosage forms may be varied according to the nature and amount of the expressed DRB1 gene product, the therapeutic benefit to be accomplished, and other such parameters. Dose ranging studies can be conducted to establish optimal therapeutic amounts of modified DRB1 peptides to be expressed by the cells. The cells should express a modified DRB1 gene product in an amount effective to significantly reduce or eliminate an immune response to a DRB1 epitope upon administration to a subject. The dosage forms may be administered at a variety of frequencies. At least one administration of the modified DRB1-expressing cells may be sufficient to generate a pharmacologically relevant response. Alternatively, at least two administrations, at least three administrations, or at least four administrations, or more, of the modified DRB1-expressing cells may be utilized to ensure a pharmacologically relevant response.

The methods described herein may further comprise expanding the modified cell, or population of cells, ex vivo after the cells are modified and prior to administration to a subject. The ex-vivo expansion of the modified cells (e.g., modified hematopoietic stem cells (HSCs)) allows efficient engraftment of the modified cells and the use of induced pluripotent stem cells (iPSCs) for screening and clinical application. Thus, this disclosure provides compositions and methods for the efficient expansion of autologous HSCs, autologous gene-modified HSCs, ESs, and iPSC-derived HSCs. Cord blood expansion methodology may be employed, which methodology utilizes Delta1 in serum free media supplemented with hematopoietic growth factors using mobilized peripheral blood CD34+ obtained from normal donors. These compositions and methods may be used in combination with one or more additional reagents to enhance the survival and proliferation of the modified hematopoietic stem/progenitor cells. These compositions and methods may employ endothelial cell co-cultures for the enhanced expansion of long-term repopulating cells, including corrected iPSC-derived HSCs.

Ex vivo expansion of modified autologous HSCs enhances the safety and effectiveness of HSC-based gene therapy by permitting the transplantation of greater numbers of appropriately modified repopulating cells to allow for rapid repopulation and ensures predominance of the modified cells in vivo.

In these methods, agents that inhibit differentiation (e.g., the Notch ligand) may be combined with compositions and methods that enhance the proliferation and survival of early stem/progenitor cells thereby achieving improved Notch-mediated ex vivo expansion. Enhanced proliferation of cord blood stem/progenitor cells may be achieved by combining the Notch ligand, Delta1, with the aryl hydrocarbon receptor inhibitor (SRI) (Boitano et al., Science 329:1345-8 (2011) or HoxB4 (Watts et al., Blood 116:5859-66 (2010) and Zhang et al., PLoS Med 3:e173 (2006)) to enhance proliferation and self-renewal of hematopoietic precursors, and with angiopoietin-like 5 to enhance their survival. Essential to the clinical application of gene therapy is the ability to expand long-term the modified, repopulating cells, assuring longevity of the corrected cell graft.

Akt-activated endothelial cells may be employed in co-culture systems to confirm expansion of the modified cells (see, Butler et al., Cell Stem Cell 6:251-64 (2011)). Expansion of gene-corrected cells depends upon endothelial cell-induced activation of Notch signaling in the hematopoietic precursors. A second critical aspect for clinical application is the genetic and epigenetic fidelity of the derived cells as compared to their normal counterparts to ensure appropriate behavior and lack of oncogenic potential in vivo. Importantly, genome-wide assessment of expanded cord blood stem/progenitor cells exhibit fidelity of the transcriptome, chromatin structure, and the DNA methylome in comparison with primary isolated cells.

Cord blood expansion methodology may utilize Delta1 in serum free media supplemented with hematopoietic growth factors using mobilized peripheral blood obtained from normal donors. Optimized ex vivo expansion conditions using established in vitro assays (immunophenotyping, growth, etc) and in vivo repopulating ability may be assessed using the NSG mouse model. Optimized conditions may be used in combination with compositions that include SRI (aryl hydrocarbon receptor inhibitor), Hox proteins, or angiopoietins to enhance the proliferation and survival of early stem/progenitor cells. Promising combinations may be evaluated in progenitor cell in vitro assays and in the immunodeficient mouse model (NSG mice) and then extended from expansion of HSC cells from normal individuals to evaluate these methods for expansion of HSC cells from subjects with RA.

The transcriptional, genetic, and epigenetic fidelity of expanded cells with their normal counterpart HSCs may be assessed using genome wide approaches to assess the oncogenic potential of the generated cells. Following growth in vivo (after infusion), cells may be used to determine whether there are functionally significant aberrations that enhance in vivo growth of any affected clone(s), thereby allowing selective expansion and detection of rare cells.

Prophylactic administration of the expressing cells may be initiated prior to the onset of RA, or therapeutic administration can be initiated after RA has developed in a subject. A "maintenance" dose may be administered to a subject after an initial administration has resulted in a reduction of DRB1 autoimmune response in the subject, for example to maintain the suppression of RA achieved after the initial dose, to prevent an undesired immune reaction in the subject, or to prevent the subject becoming a subject at risk of experiencing an undesired immune response or an undesired level of an immune response. The maintenance dose may be the same dose as the initial dose the subject received. Alternatively, the maintenance dose may be a lower dose than the initial dose, including for example, a maintenance dose that is about ¾, about ⅔, about ½, about ⅓, about ¼, about ⅛, about 1/10, about 1/20, about 1/25, about 1/50, about 1/100, about 1/1,000, about 1/10,000, about 1/100,000, or about 1/1,000,000 (weight/weight) of the initial dose.

In the therapeutic methods of this disclosure, the cells and compositions provided herein may be used in conjunction with established means of treating RA. RA treatment protocols are known in the art and are generally described at e.g., arthritis.org/about-arthritis/types/rheumatoid-arthritis/treatment.php. Administration of the modified cells as described herein can be conducted before, after, and/or concurrently with established RA treatment protocols and/or variations thereof. For example, the methods of this disclosure may increase the effectiveness of established RA treatment protocols (e.g., the degree and/or likelihood of successful treatment) and/or reduce associated costs or side effects. The methods of this disclosure may allow established RA treatment protocols to be beneficially modified, e.g., to decrease the frequency, duration, and/or dose of RA treatment administration.

The modified cells of this disclosure may be combined with, or administered with, immunosuppressive compounds capable of inducing adaptive regulatory T cells. In one embodiment, the immunosuppresive compound(s) may include, but are not limited to, IL-10, TGF-β, and/or rapamycin and/or other "limus" compounds, including but not limited to biolimus A9, everolimus, tacrolimus, and zotarolimus, and/or combinations thereof.

EXAMPLES

Example 1

Ex Vivo Gene Modification

Examples are provided of an ex vivo gene modification strategies that can be performed without the use of viral vectors. Genetic materials are delivered to modify DRB1*04:01 allele to express a protein having a glutamic acid residue at position 71 (DRB1*04:01$^{K71E}$) in HSCs derived from a human RA patient using electroporation and Cas9 nuclease.

Use of autologous cells is an attractive therapy as clinically relevant levels of DRB1 proteins may be more readily produced by expansion of large populations of cells ex vivo, followed by reintroduction into the patient. Modification of codon 71 in the DRB1*04 alleles residing in HSCs derived from a patient with severe RA associated with the DRB1*04:01 allele is effected using electroporation to introduce into a HSC cell of the subject (i) a guide RNA sequence complementary to at least a portion of the DRB1*04:01 allele, (ii) a Cas9 protein, (iii) a template nucleic acid comprising at least a portion of an HLA-DRB1 allele, wherein the guide RNA sequence binds to the target nucleic acid sequence (portion of the DRB1*04:01 allele) and the Cas9 protein cleaves the target nucleic acid sequence, and the portion of the HLA-DRB1 allele in the template nucleic acid is substituted into the target nucleic acid.

The use of viral-free methods to derive autologous cells of various phenotypes and to stably introduce genetic information into the genome is attractive. These methods can be effectively used to successfully modify the DRB1*04:01 allele to prevent or treat RA in a subject.

An example of a sequence that can be targeted includes a sequence within the DRB1*04:01 allele that includes codon 71 which encodes a lysine residue.

Electroporation (AMAXA Nucleofection system) and chemical transfection (with a commercial reagent optimized to this cell type) are used as transfection methods for the HSC cells. A plasmid containing the green fluorescent protein (GFP) gene is introduced into the cells using both methods. The cells are analyzed by fluorescent microscopy to obtain an estimate of transfection efficiency, and the cells are observed by ordinary light microscopy to determine the health of the transfected cells. Any transfection method that gives a desirable balance of high transfection efficiency and preservation of cell health in the HSC cells may be used. The guide RNA and the gene modification plasmid is then introduced into the HSC cells using a transfection method.

The HSCs with modified DRB1 gene are differentiated into hematopoietic cells and expanded using well established protocols.

Characterization of the genomic DNA at the modified DRB1 loci, as well as the mRNAs and expression products synthesized by the HSC cells, before and after electroporation, is performed.

The efficiency of transfection for expression and secretion of modified DRB1*04 gene products can be assessed in the various cell types before and after transfection. Genomic DNA is isolated from cells before and after transfection. Purified genomic DNA is used as template for PCR. Primers are designed for amplification from a DRB1-specific primer only in unmodified cells, and amplification from the modification-specific primer only in modified cells. RT-PCR can specifically detect and quantify the mRNA DBR1 transcripts from normal and modified cells. Flow-cytometry based assays may also be used for DRB1*04:01 gene product in populations of treated cells.

Example 2

Protocol for Factor VIII Gene Modification in Humans

Obtaining a Blood Sample: A protocol for modification of the DRB1*04:01 allele in blood outgrowth endothelial cells (BOECs) is described in the following example. First, a blood sample is obtained, with 50-100 mL of patient blood samples obtained by venipuncture and collection into commercially-available, medical-grade collecting devices that contain anticoagulants reagents, following standard medical guidelines for phlebotomy. Anticoagulant reagents that are used include heparin, sodium citrate, and/or ethylenediaminetetraacetic acid (EDTA). Following blood collection, all steps proceed with standard clinical practices for aseptic technique.

Isolating Appropriate Cell Populations from Blood Sample: Procedures for isolating and growing blood outgrowth endothelial cells (BOECs) have been described in detail by Hebbel and colleagues (Lin, Y., Weisdorf, D. J., Solovey, A. & Hebbel, R. P. Origins of circulating endothelial cells and endothelial outgrowth from blood. J Clin Invest 105, 71-77 (2000)). Peripheral blood mononuclear cells (PBMCs) are purified from whole blood samples by differential centrifugation using density media-based separation reagents. Examples of such separation reagents include Histopaque-1077, Ficoll-Paque, Ficoll-Hypaque, and Percoll. From these PBMCs multiple cell populations can be isolated, including BOECs. PBMCs are resuspended in EGM-2 medium without further cell subpopulation enrichment procedures and placed into 1 well of a 6-well plate coated with type I collagen. This mixture is incubated at 37° C. in a humidified environment with 5% CO2. Culture medium is changed daily. After 24 hours, unattached cells and debris are removed by washing with medium. This procedure leaves about 20 attached endothelial cells plus 100-200 other mononuclear cells. These non-endothelial mononuclear cells die within the first 2-3 weeks of culture.

Cell Culture for Growing Target Cell Population: BOECs cells are established in culture for 4 weeks with daily medium changes but with no passaging. The first passaging occurs at 4 weeks, after approximately a 100-fold expansion. In the next step, 0.025% trypsin is used for passaging cells and tissue culture plates coated with collagen-I as substrate. Following this initial 4-week establishment of the cells in culture, the BOECs are passaged again 4 days later (day 32) and 4 days after that (day 36), after which time the cells should number 1 million cells or more.

In Vitro Gene Modification: In order to affect gene modification in BOECs, cells are transfected with 0.1-10 micrograms per million cells of a vector encoding a Cas9 nuclease, a template nucleic acid, and a guide RNA encoding crRNA comprising the coding sequence GGACCUCGUCUUCGCCCGGCGCC (SEQ ID NO:1) that targets codon 71 in the HLA allele DRB1*04:01. Transfection is done by electroporation, liposome-mediated transfection, polycation-mediated transfection, commercially available proprietary reagents for transfection, or other transfection methods using standard protocols. Following transfection, BOECs are cultured as described above for three days.

Selection of Gene-Modified Clones: Using the method of limiting serial dilution, the modified BOECs are dispensed into clonal subcultures, and grown as described above. Cells are examined daily to determine which subcultures contain single clones. Upon growth of the subcultures to a density of >100 cells per subculture, the cells are trypsinized, resuspended in medium, and a 1/10 volume of the cells is used for colony PCR. The remaining 9/10 of the cells are returned to culture. Using primers that detect productively modified DRB1 genes, each 1/10 volume of colonies are screened by PCR for productive gene modification. Colonies that exhibit productive DRB1 gene modification are further cultured to increase cell numbers. Each of the colonies may be selected for further culturing by screening for possible deleterious off-site mutations. The colonies exhibiting the least number of off-site mutations are chosen for further culturing.

Preparation of Cells for Re-Introduction into Patients by Conditioning and/or Outgrowth: Prior to re-introducing the cells into patients, the BOECs are expanded in culture to increase the cell numbers.

Injection of Gene-Modified BOECs into Patients: BOECs that have been chosen for injection into patients are resuspended in sterile saline at a dose and concentration that is appropriate for the weight and age of the patient. Administration of the cell sample is performed as an autologous bone marrow transplant using standard clinical practices.

Example 3

Design and Testing of Guide Sequences for the CRISPR/Cas9 System

The inventors used CRISPOR (crispor.tefor.net) to design, evaluate, and clone guide sequences for the CRISPR/Cas9 system. The sequence for HLA-DRB1*04:01 was analyzed using the *Homo sapiens* genome and a protospacer adjacent motif (PAM) specific for SpCas 9 where the 20 base pair sequence of the guide needs to be followed with NGG. Multiple guide sequences with a specificity score greater than 50 were identified, but only three guides spanned the target region of DRB1*04:01. One guide had a high GC content and was therefore eliminated, but the other two guide sequences (185/rev and 208/fwd) were selected for further evaluation:

Guide 185/rev: 5'cggcccgcttctgctccagg 3' (SEQ ID NO:2)
Guide 208/fwd: 5'cctggagcagaagcgggccg 3' (SEQ ID NO:3)

Figure 2:
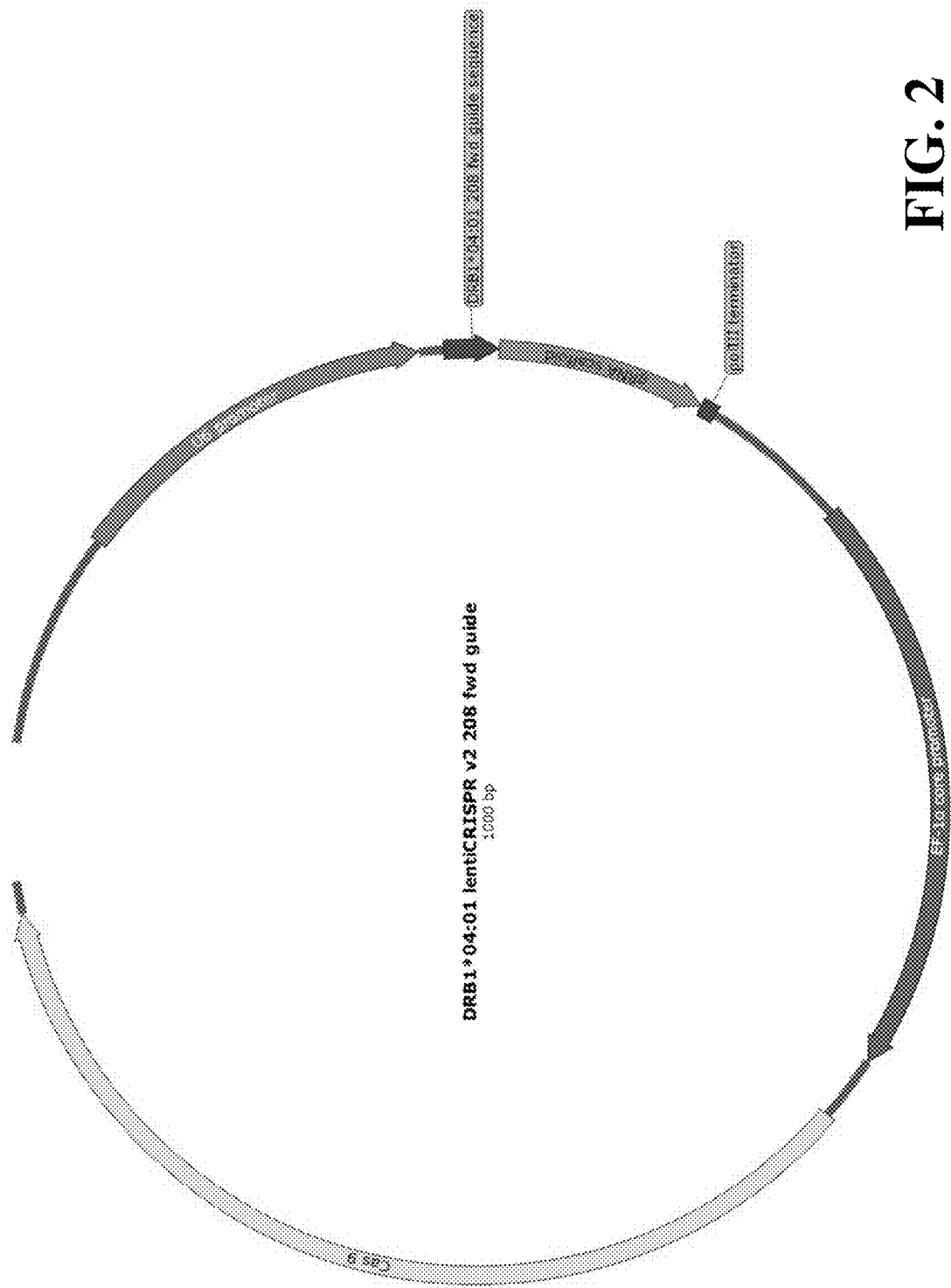
FIG. 2 is a map of another lentiviral plasmid encoding a DRB1*04:01 guide sequence of this disclosure.

Guide 185/rev had a specificity score of 70 with 142 predicted off-targets. Guide 208/fwd had a specificity score of 68 with 252 predicted off-targets. Each guide was cloned into the lentiCRISPR v2 plasmid (Addgene plasmid #52961). The lentivirus v2 DRB1*04:01 185rev and 208fwd plasmids (FIGS. 1 and 2, respectively) were grown, purified, and sequenced for verification.

Lentiviral particles were prepared using TransIT-Lenti-LT-1 transfection reagent (Mirus). Briefly, 293TN cells were seeded at $2.5 \times 10^6$ in 10 ml of DMEM without antibiotics, 10% FCS and incubated at 37° C. overnight. The next day, the cells were transfected (when cells are 70% confluent). The plasmid DNA and LT-1 reagent were brought to room temperature and OptiMEM medium warmed to 37° C. 15 μl of LT-1 reagent was added dropwise to 500 μl OptiMEM in a separate 1.5 ml Eppendorf tube. The tube was mixed and incubated for 5 minutes. Transfection reactions were set up in 1.5 ml eppendorf tubes containing 2 μg Lentivector DNA, 3 μg psPAX2 helper plasmid (Addgene), 1.5 μg pMD2.G helper plasmid (Addgene) in a final volume of 50 μl using OptiMEM. The 50 μl containing DNA was added to the LT-1 tube dropwise, mixed, and incubated at room temperature for 30 minutes. After incubation, the contents of the tube were added dropwise to the 10 cm dish that contained 293TN cells. Plates were rocked to mix and incubated at 37° C. overnight in a secondary containment vessel. The next day, the media was changed without disturbing the cells and replaced with fresh media. On day 4, the supernatant was harvested and 0.5 ml aliquots stored at −80° C.

T2 cells expressing DRB1*04:01, *01:01, *08:01 or *04:02 were transduced with lentivirus using polybrene. Briefly, $2 \times 10^6$ T2 cells were plated in 6 well plates in 1 ml of media. 200 μl of virus was added to the well with 12 μl of 100× polybrene. The cells were incubated for 6-10 hours and then 3 ml of complete media added to bring the final concentration of cells to 0.5×10⁶/ml. The next day, puromycin was added to the culture at a final concentration of 1 μg/ml. Antibiotic resistant cells were grown and stained with an anti-HLA-DR antibody to look for the loss of HLA expression due to CRISPR/Cas9 editing and non-homologous end joining repair.

Loss of HLA-DR expression was observed in T2-DRB1*04:01 cells transduced with 208/fwd or 185/rev lentivirus but not in the control cell lines. The non-transduced DRB1*04:01 cell line went from 95% HLA-DR expression to 20% or 12% after Lentivirus transduction with the 208/fwd guide or 185/rev guide, respectively. The cell lines expressing T2-DRB1*04:02 and T2-DRB1*08:01 showed no loss of HLA-DR expression demonstrating specificity of the tested guide RNAs. Loss of HLA-DR expression was also observed in the T2-DRB1*01:01 cells (94% to 71% or 23.5% for 208/fwd or 185/rev, respectively). This was expected because DRB1*01:01 has only one nucleotide difference (at position 71) as compared to DRB1*04:01 in this region. Thus, the guide RNAs designed for DRB1*04:01 were also able to target DRB1*01:01. The DRB1*01:01 allele is also associated with RA susceptibility.

Flow cytometry was used to sort for the population of cells that had lost HLA-DR expression. Genomic DNA was prepared and sequenced from this population of cells for both DRB1*04:01 and DRB1*01:01. The loss of expression was confirmed on the DNA level as deletions or insertions of nucleotides that caused the gene to be out of frame and no longer expressed. The DRB1*04:02 and DRB1*08:01 control cell lines that had received CRISPR lentivirus but exhibited no loss of HLA-DR expression were also sequenced. No changes were found in the DNA sequence indicating that the guide RNA sequences are specific and did not cause Cas9 editing of DRB1*04:02 or DRB1*08:01.

Example 4

HLA-DR Expression Following CRISPR/Cas9 Editing

Nucleofection (Lonza) was used to introduce the 208/fwd guide or 185/rev guide RNAs and Cas 9 protein into cell lines. Synthetic guide RNAs for 208/fwd and 185/rev were purchased from Synthego. Each guide plus Synthego Cas9-2NLS protein was mixed to form Cas9:sgRNA RNP complexes at a ratio 1:5.25. The RNP complexes were nucleofected into T2-DRB1*04:01 cell lines to evaluate editing efficiency. Non-transfected cells (FIG. 3A) and scrambled sgRNA (FIG. 3B) were tested as negative controls.

Figures 3C, 3D:
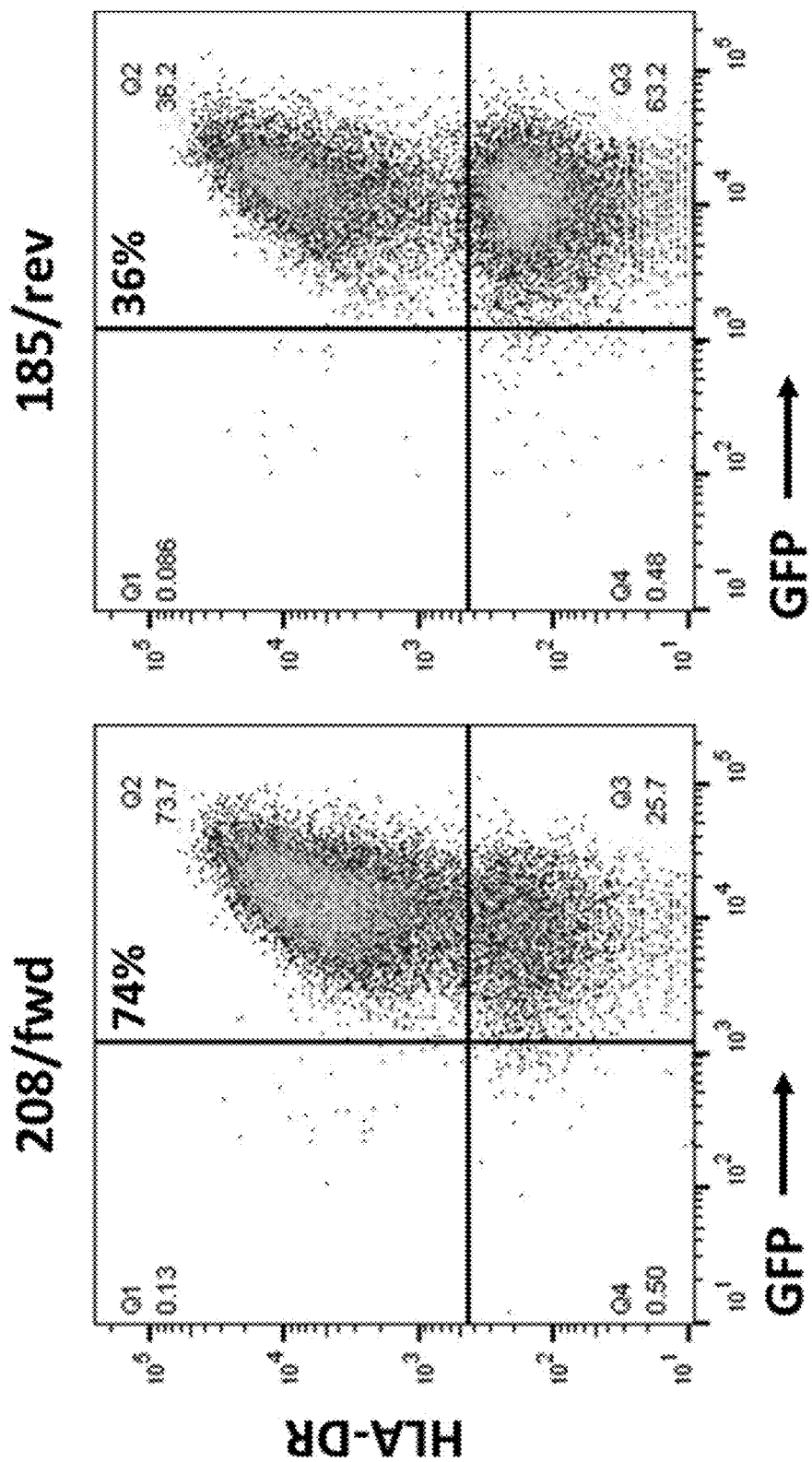

The loss of HLA-DR expression was seen in the cells that received either the 208/fwd:Cas9 RNPs (FIG. 3C) or the 185/rev:Cas9 RNPs (FIG. 3D). Cells that received the negative control sgRNA showed no loss of HLA-DR expression (FIG. 3B). Additionally, nucleofection of T2 cell lines expressing DRB1*04:02 and DRB1*08:01 showed no loss of HLA-DR expression. The T2-DRB1*01:01 cells did show some loss of HLA-DR expression but to a lesser degree than what was seen with lentivirus transduction.

Example 5

Transgenic Mice

The inventors have also developed a transgenic mouse that expresses only human HLA-DRB1*04:01$^{K71E}$ to compare antigen-specific T cell responses to arthritogenic peptides in HLA-DRB1*04:01 transgenic mice versus HLA-DRB1*04:01$^{K71E}$ transgenic mice. These mice are used to demonstrate that increased susceptibility for RA in individuals who express DR1*04:01 is due to the presence of $K^{71}$, which promotes binding of citrullinated peptides and collagen by interfering with native peptide binding. Thus, transgenic mice that express DR1*04:01$^{K71E}$ will not generate strong T cell responses to citrullinated peptides and collagen. This mouse also demonstrates that stem cells from DRB1*04:01$^{K71E}$ mice transplanted into HLA-DRB1*04:01 mice do not cause graft-vs-host disease.

Throughout this application, various publications are referenced. The disclosures of these publications in their entireties are hereby incorporated by reference into this application, to the extent allowed by law.

The foregoing disclosure is sufficient to enable one skilled in the art to practice the invention. The present invention is not to be limited in scope by the constructs described, because the described embodiments are intended as illustrations of certain aspects of the invention and any constructs that are functionally equivalent are within the scope of this invention.

What is claimed is:

1. A composition comprising:
an autologous hematopoietic cell containing a modified HLA-DRB1*04:01 allele, wherein codon 71 of the HLA-DRB1*04:01 allele has been gene edited from coding for lysine to coding for glutamic acid.

2. The composition of claim 1, wherein the autologous hematopoietic cell produces a functional HLA-DRB1 gene product.

3. The composition of claim 1, wherein the autologous hematopoietic cell comprises a CD34+ cell.

4. The composition of claim 1, wherein the gene editing is mediated by clustered regularly interspaced short palindromic repeats (CRISPR) and CRISPR associated (Cas) nucleases.

5. The composition of claim 4, wherein the Cas nuclease is a Cas9 nuclease.

* * * * *

SEQUENCE LISTING

```
<160> NUMBER OF SEQ ID NOS: 3

<210> SEQ ID NO 1
<211> LENGTH: 23
<212> TYPE: RNA
<213> ORGANISM: Artificial Sequence
<220> FEATURE:
<223> OTHER INFORMATION: Synthetic Guide Sequence

<400> SEQUENCE: 1
ggaccucguc uucgcccggc gcc                                            23

<210> SEQ ID NO 2
<211> LENGTH: 20
<212> TYPE: DNA
<213> ORGANISM: Artificial Sequence
<220> FEATURE:
<223> OTHER INFORMATION: Synthetic Guide Sequence
```

```
<400> SEQUENCE: 2
cggcccgctt ctgctccagg                                               20

<210> SEQ ID NO 3
<211> LENGTH: 20
<212> TYPE: DNA
<213> ORGANISM: Artificial Sequence
<220> FEATURE:
<223> OTHER INFORMATION: Synthetic Guide Sequence

<400> SEQUENCE: 3
cctggagcag aagcgggccg                                               20
```